United States Patent [19]

Chappel

[11] Patent Number: 5,272,071
[45] Date of Patent: Dec. 21, 1993

[54] METHOD FOR THE MODIFICATION OF THE EXPRESSION CHARACTERISTICS OF AN ENDOGENOUS GENE OF A GIVEN CELL LINE

[75] Inventor: Scott C. Chappel, Jamaica Plain, Mass.

[73] Assignee: Applied Research Systems Ars Holding N.V., Curacao, Netherlands Antilles

[21] Appl. No.: 893,447
[22] PCT Filed: Dec. 21, 1990
[86] PCT No.: PCT/US90/07642
  § 371 Date: May 28, 1992
  § 102(e) Date: May 28, 1992

Related U.S. Application Data

[63] Continuation-in-part of Ser. No. 454,783, Dec. 22, 1989, abandoned.
[51] Int. Cl.$^5$ .................. C12N 15/00; C12N 5/00; C12P 21/06
[52] U.S. Cl. .................. 435/172.3; 435/172.1; 435/69.1; 435/320.1; 435/252.3; 435/6; 435/33; 435/34; 435/42; 536/23.1; 536/24.3
[58] Field of Search .................. 435/172.3, 172.1, 69.1, 435/320.1, 252.3; 536/23.1, 24.3

[56] References Cited

U.S. PATENT DOCUMENTS 4,950,599 8/1990 Bertling .................. 435/172.3

FOREIGN PATENT DOCUMENTS 0278659 8/1988 European Pat. Off. .
320500 6/1989 European Pat. Off. .
88/05077 7/1988 World Int. Prop. O. .
89/09256 10/1989 World Int. Prop. O. .
90/11354 1F/1990 World Int. Prop. O. .
90/14092 11/1990 World Int. Prop. O. .
91/02070 2/1991 World Int. Prop. O. .
91/06666 5/1991 World Int. Prop. O. .

OTHER PUBLICATIONS

Railbaud, O. et al., "A technique for inegratrating any DNA fragment into the chromosome of Escherichia Gene", vol. 29, No. ⅓, Jun. 1984, pp. 231-241.
Janniere et al., "Stable gene amplification in the chromosome of Bacillus subtilis", Gene, vol. 40, No. 1, 1985, pp. 47-55.
Zhu, J. et al., "Construction of stable laboratory and industrial yeast expressing a foreign gene by integrative transformation using a dominant selection system", Gene, vol. 50, Nos. 1-3, 1986, pp. 225-237.
Le Mouellic, et al., "Targeted replacement of the homeobox gene Hox-3.1 by the Escherichia coli lacZ in mouse chimeric embryos," Proc. Natl. Acad. Sci. USA 87:4712-4716 (1990).
Mansour et al., "Disruption of the proto-oncogene int-2 in mouse embryo-derived stem cells: a general strategy for targeting mutations to non-selectable genes", Nature 336(24):348-52 (1988).
Larsen et al., "Repression mediates cell-type-specific expression of the rat growth hormone gene", Proc. Natl. Acad. Sci. USA 83:8283-8287 (1986).
Brent et al., "Functional Characterization of the Rat Growth Hormone Promoter Elements Required for Induction by Thyroid Hormone with and without a Co-transfected β Type Thyroid Hormone Receptor," J. Biol. Chem. 264(1):178-182 (1989).
Johnson, et al., "Targeting of Nonexpressed Genes in Embryonic Stem Cells Via Homologous Recombination", Science 245:1234-1236 (1989).

Primary Examiner—Robert A. Wax
Assistant Examiner—Miguel Escallon
Attorney, Agent, or Firm—Browdy and Neimark

[57] ABSTRACT

Normally transcriptionally silent genes in a cell line or microorganism may be activated for expression by inserting a DNA regulatory element which is capable of promoting the expression of a normally expressed gene product in that cell or which is promiscuous, the regulatory element being inserted so as to be operatively linked with the normally silent gene in question. The insertion is accomplished by means of homologous recombination by creating a DNA construct including a segment having a DNA segment of the normally silent gene (targeting DNA) and the DNA regulatory element to induce gene transcription. The technique is also used to modify the expression characteristics of any endogenous gene of a given cell line or microorganism.

58 Claims, 14 Drawing Sheets

FIG. 2A
RANDOM INTEGRATION
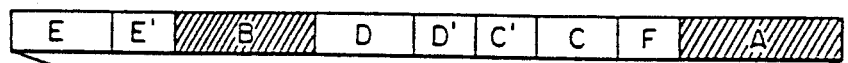
↓ RANDOM INTEGRATION
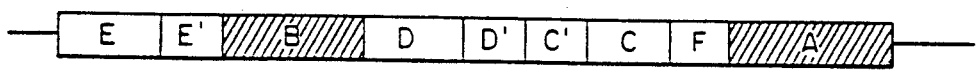
FIG. 2B
HOMOLOGOUS RECOMBINATION
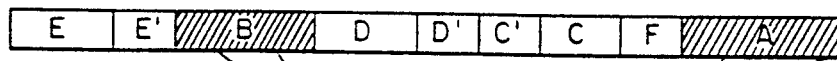
↓ HOMOLOGOUS RECOMBINATION
TRANSCRIPTION

HOMOLOGOUS RECOMBINATION CONSTRUCT FOR RAT TSH BETA

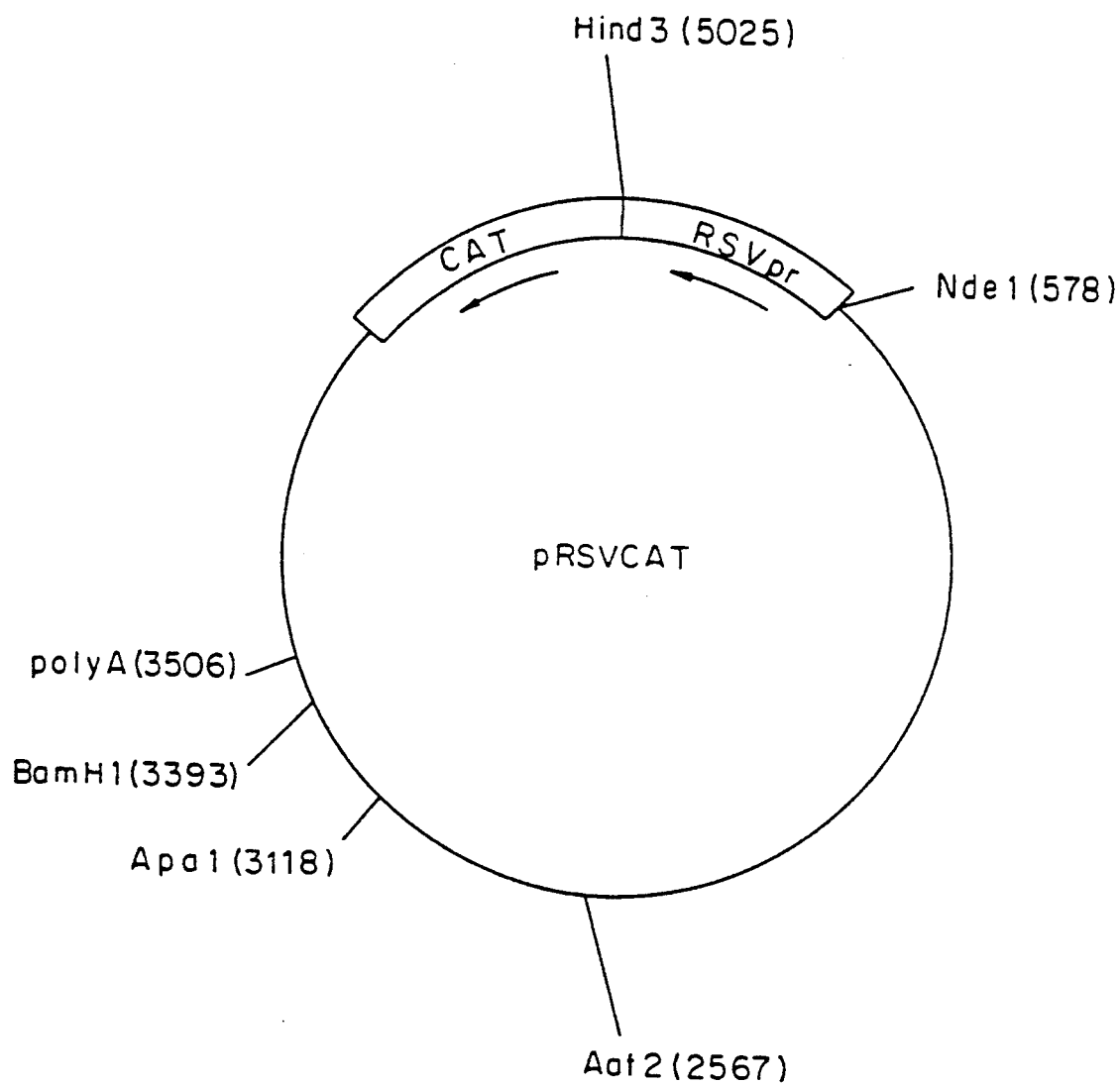
FIG. 5
ARROW INDICATES SENSE DIRECTION

* SITE NO LONGER EXISTS
ARROW INDICATES SENSE DIRECTION

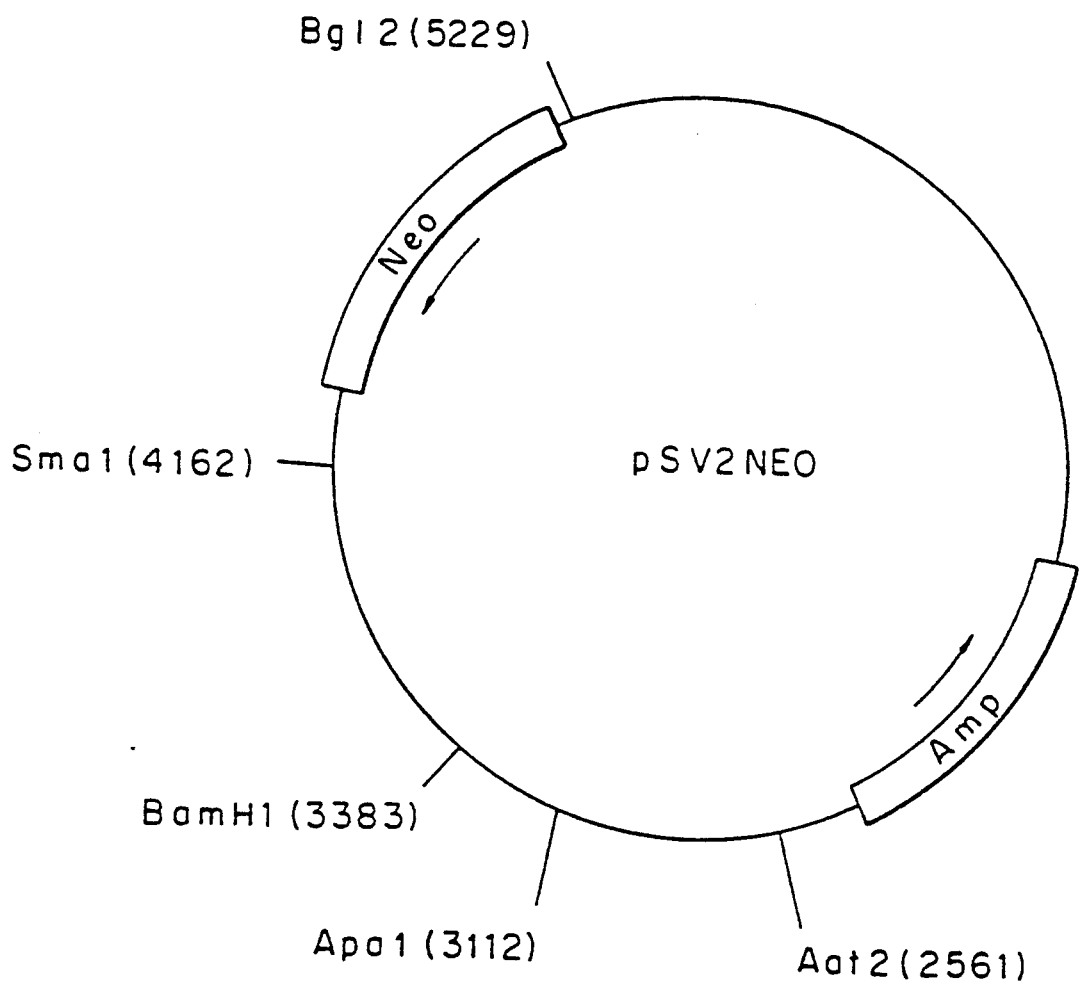
FIG. 7
ARROW INDICATES SENSE DIRECTION
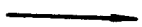

*SITE NO LONGER EXISTS
ARROW INDICATES SENSE DIRECTION

FIG. 9
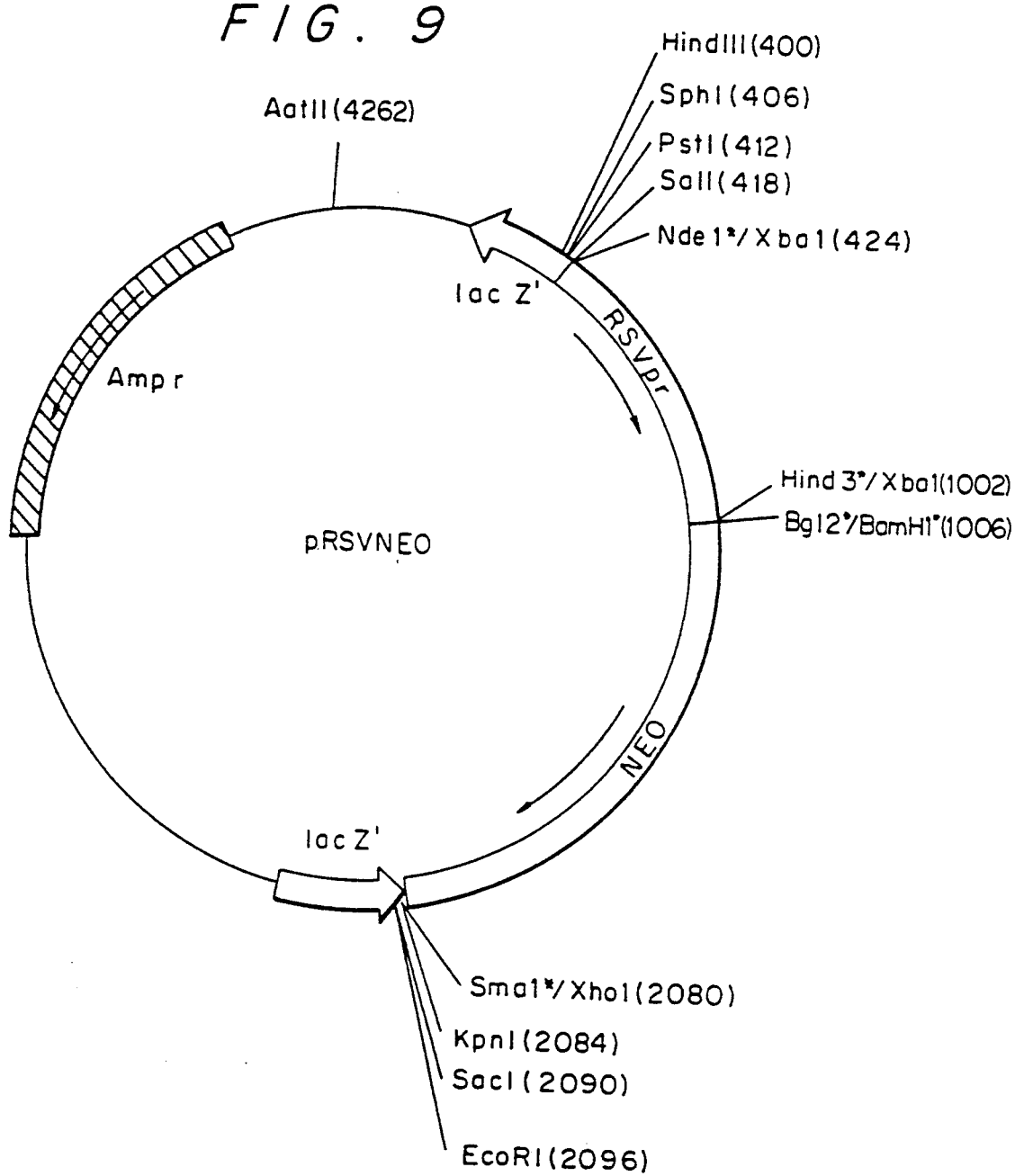
* SITE NO LONGER EXISTS
ARROW INDICATES SENSE DIRECTION

* SITE NO LONGER EXISTS
ARROW INDICATES SENSE DIRECTION

RAT TSH BETA

* SITE NO LONGER EXISTS
ARROW INDICATES SENSE DIRECTION

*SITE NO LONGER EXISTS
ARROW INDICATES SENSE DIRECTION

FIG. 14
LOCATION OF PRIMERS FOR PCR AMPLIFICATION OF TSH BETA

5'
ggcacgcctctgaatgtggaaaggacacttatgagctctgtggtctttccctctgattt ag CATGAATGCTGTCGTTCTCTTTTCCGTGCTTTTCGCTCTTGCTTGTGGGCAAGTGT

```
                          5'            TSHB5       3'
                          AGTATATGATGTACGTGGACAGG
CATCGTTTTGTATTCCCACTG AGTATATGATGTACGTGGACAGGAGAGAGTGTGCCTAC
                      ************************************
```

TGCCTGACCATCAACACCACC ATCTGCGCTGGGTATTGTATGACACGG gtatgttggt
************************************************* cactgcgtttcttttagctgtaaattgtacaggtctaaagttgtctgttaatatttag aaaggaagtgggataaatcatagtctcctcttgggaagccaagcacactgctttcaga attaattatgtcattctacacagaaaaagtacagatacattgtaacagtttaccca aagtgtttgttctgctcaatggtagatgagaagaaagtgtccttttttgtctctgaggg gttaagtgtagatgtgtgggtaacagagctcaggagtcctttaagatcatcaggaaaca aagggatattagtcattctattacactaagttgcatgcagtttatcatgttaagatctc ttttcttccacag GATATCAATG GCAAACTGTTTCTTCCCAAGTACGCACTCTCTCAG
              ***************************************

GATGTCTGTACATACAGAGACTTC ACCTACAGAACGGTGGAAATACCGGGATGCCCACA
********************************************************

CCATGTTGCTCCTTATTTCTCCTACCCCGTTGCCCTGAGCTGCAAGTGTGGCAAGTGTA
*********************************************************

```
                          GGACTCGACGTTCACACCGTTCAC
                       3'           TSHB3        5'
```

ACACTGACTACAGCGACTGTACACACGAGGCTGTCAAAACCAACTACTGCACCAAGCCA

CAGACATTCTATCTGGGGGGATTTTCTGGTTAACTGTAATGGCAATGCAATCTGGTTAA

ATGTGTTTACCTGGAATAGAACTAATAAAATATCATTGAT atgtcttgcctgccattt aatccataggcacatccacaaggcattagagagcttacacaactttagaagcagaggcg

3'

EXONS 2 AND 3 ARE IN CAPITAL LETTERS

247 BP AMPLIFIED FRAGMENT UNDERLINED BY *

METHOD FOR THE MODIFICATION OF THE EXPRESSION CHARACTERISTICS OF AN ENDOGENOUS GENE OF A GIVEN CELL LINE

CROSS-REFERENCE TO RELATED APPLICATIONS

The present application is the national phase filing of PCT application Ser. No. PCT/US90/07642, filed Dec. 21, 1990, and is a continuation-in-part of U.S. application Ser. No. 07/454,783, filed Dec. 22, 1989, now abandoned.

FIELD OF INVENTION

The present invention relates to a process for the modification of the expression characteristics of a gene which is naturally present within the genome of a stable cell line or cloned microorganism. In the preferred embodiment, the present invention relates to a process for the activation and expression of a gene that is present within a stable cell line and normally transcriptionally silent or inert. As a result, the protein product of that gene is expressed. This phenomenon occurs without transfecting the cell with the DNA that encodes the product. Rather, the resident gene coding for the desired product is identified within a cell and activated by inserting an appropriate regulatory segment through a technique called homologous recombination. Positive and/or negative selectable markers can also be inserted to aid in selection of the cells in which proper homologous recombination events have occurred. As an additional embodiment, a specified gene can be amplified for enhanced expression rates, whether that gene is normally transcriptionally silent and has been activated by means of the present invention, or endogenously expresses product.

BACKGROUND OF THE INVENTION

It is well known that each cell within an organism contains the genetic information that encodes all of the proteins found within that organism. However, only a very small percentage of the genes present within a given cell type is actually transcribed. The intracellular mechanisms that regulate the array of genes to be transcribed are now understood. Cell specific proteins present within the nucleus interact with DNA regulatory Segments that are linked with particular genes. This interaction of nuclear proteins with DNA regulatory sequences is required for gene transcription. This results in mRNA biosynthesis and ultimate expression of the encoded protein (Mitchell and Tjian, *Science*, 245:371, 1989).

These DNA regulatory segments or elements for each gene lie upstream from and, in some cases, within or even downstream of the coding regions. Through an interaction with cell specific nuclear proteins, DNA regulatory segments affect the ability of RNA polymerase, the rate limiting enzyme in protein expression, to gain access to the body of the gene and synthesize a mRNA transcript. Thus, these DNA segments and the resident nuclear proteins play a critical role in the regulation of expression of specific genes (Johnson and McKnight, *Ann. Rev. Biochem.*, 58:799, 1989).

The DNA regulatory segments are binding sites for the nuclear proteins. These nuclear proteins attach to the DNA helix and apparently alter its structure to make the desired gene available for RNA polymerase recognition, which facilitates gene transcription. The expression of these cell specific regulatory proteins determines which genes will be transcribed within a cell and the rate at which this expression will occur. As an example of the specificity of this system, pituitary cells but not liver cells express pituitary proteins, even though the genes for the pituitary proteins are present within all liver cells. Nuclei of the liver cells do not contain the specific DNA binding proteins which interact with the elements of pituitary genes resident within the liver cells.

CURRENT METHODS EMPLOYED TO EXPRESS PROTEINS USING RECOMBINANT DNA TECHNOLOGY

With the knowledge that specific DNA regulatory sequences are required to activate gene transcription within a particular cell type, scientists have expressed foreign genes within a particular cell type through genetic engineering. In general, DNA regulatory segments that are recognized by the cell's nuclear proteins are placed upstream from the coding region of a foreign gene to be expressed. In this way, after insertion into the cell, foreign DNA may be expressed since the cell's nuclear regulatory proteins now recognize these DNA regulatory sequences. This technology has been employed to produce proteins that have been difficult to obtain or purify from natural sources by traditional purification strategies.

In addition to the recognizable DNA sequences and the gene of interest, a selectable marker is attached to the DNA construction. In this way, only the cells that have taken up the DNA survive following culture in a selectable medium. For example, the gene for neomycin resistance may be included in the expression vector. Following transfection, cells are cultured in G418, a neomycin antibiotic that is lethal to mammalian cells. If however, the cells have acquired the neomycin resistance gene, they will be able to withstand the toxic effects of the drug. In this way, only the cells that have taken up the transfected DNA are maintained in culture. It is understood that any selectable marker could be used as long as it provided for selection of cells that had taken up the transfected DNA. It is further understood that there is no criticality as to the specific location of the inserted genetic material within the cell. It is only important that it be taken up somewhere within the nucleus as both the regulatory segment and the foreign gene (as well as the selectable marker) are inserted together.

DEFICIENCIES IN THE CURRENT METHODS OF GENE EXPRESSIONS

While the above techniques have been instrumental in exploiting the power of genetic engineering, they have not always been the most efficient methods to express genes. This is due to the fact that insertion of DNA into the nucleus of a cell line is usually accomplished through a technique known as transfection. DNA that has been engineered for expression in the cell line of interest is precipitated and the cell membrane is solubilized to allow entry of the DNA. As indicated above, the exact site into which the DNA incorporates into the genome is never predictable; indeed the DNA may remain episomal (not integrated into the genome). This results in the unpredictability of both the level of expression of the protein produced and the stability of the cell line.

A second shortcoming of this technique is the fact that the construction of the expression vector is extremely difficult when the gene of interest is relatively large (greater than 5-10 kilobases). Many of the proteins expressed by recombinant DNA technology have been encoded by cDNAs rather than much larger genomic clones. This is done to reduce the overall size of the insert. While the use of cDNAs makes genetic engineering more convenient, rates of gene transcription and protein production may suffer as a result. It has recently been shown that expression levels are sometimes greatly enhanced through the use of genomic rather than cDNA inserts (Brinster et al., *Proc. Natl. Acad. Sci.*, 85:836-840, 1988, and Chung and Perry, *Mol. Cell. Biol.*, 9:2075-2082, 1989). Although the mechanisms responsible for this observation are not well understood, it is known that in certain situations enhancer elements present within introns can improve the transcriptional efficiency of the gene. There is also evidence that introns, or the splicing events which result from the presence of introns, may have an effect on the RNA processing events which follow the initiation of transcription (Buchman and Berg, *Mol. Cell. Biol.*, 8:4395-4405, 1988). This may stabilize the transcript thereby improving the rate of mRNA accumulation. In the above cited Brinster et al paper, it is also postulated that the position of the introns within the gene may be important for phasing of nucleosomes relative to the promoter. The influence of various regulatory elements on transcription of eukaryotic genes is discussed in Khoury et al, *Cell*, 33:313-14 (1983), Maniatis et al, *Science*, 236:1237-45 (1987) and Muller et al, *Eur. J. Biochem.*, 176:485-95 (1988).

Thirdly, to gain entry into the nucleus, the transfected DNA, including the entire coding region of the foreign gene, must traverse the cytoplasm following entry through the permeabilized plasma membrane of the cell. During that time, the DNA may come in contact with lysosomal enzymes which may alter or completely destroy the integrity of the DNA. Thus, the coding region of the DNA may not be identical to that which was transfected.

The novel method of gene activation and/or expression modification that we describe below cannot result in the production of mutant forms of the desired protein, since the coding region of the desired gene is not subjected to enzymatic modifications.

In summary, a large amount of the DNA transfected into the cell using traditional techniques, and particularly the coding region thereof, will not be faithfully transcribed. It may be degraded prior to entry into the nucleus, enzymatically perturbed so that it will not encode the entire desired protein or it may not contain all of the necessary regulatory segments to allow for transcription. It may be inserted into a portion of the genome that prevents transcription. If the cDNA is transcribed, the protein of interest may not be produced efficiently due to the omission of introns which may contain enhancers or enable efficient mRNA processing. Finally, it may remain episomal, promote protein production but be unstable as the cell population grows through cell division.

It would be most desirable to develop a method of induction of gene expression that would produce a cell line that has incorporated the positive attributes of the existing methods but somehow circumvents the unattractive features. It would further be desirable to be able to express or modify endogenous expression of particular genes in the cell type of choice. It is further desired to be able to take advantage of the potential benefits that may be afforded by a complete genomic sequence which may include cryptic transcriptional enhancers that may reside within introns, by appropriate placement of introns for proper nucleosome phasing or by more efficient mRNA processing events. These advantages are ordinarily not enjoyed in recombinant DNA expression methods due to the size of the gene. If one were able to express a gene that is already resident in the genome, i.e., an endogenous gene, cell line stability and expression rates would become more consistent and predictable.

SUMMARY OF THE INVENTION

Accordingly, it is an object of the present invention to eliminate the above-noted deficiencies in the prior art.

It is another object of the present invention to provide a method of regulation and/or amplification of gene expression that incorporates the positive attributes of recombinant gene technology but circumvents the unattractive features.

It is a further object of the present invention to provide a method for expressing specific genes present but normally transcriptionally silent in a cell line of choice.

It is yet a further object of the present invention to provide a method for expressing proteins which takes full advantage of complete genomic sequences that are responsible for mRNA accumulation and/or transcription.

It is still another object of the present invention to provide a method of modifying the expression characteristics of a gene of interest by inserting DNA regulatory segments and/or amplifying segments into the genome of a stable cell line or cloned microorganism upstream of, within, or otherwise proximal to the native gene of interest.

It is still a further object of the present invention to provide a method for modifying the expression characteristics of a gene which is naturally present within the genome of a stable cell line or cloned microorganism and at the same time insert characteristics which will aid in the selection of cells which have been properly modified.

It is yet another object of the present invention to provide a genome having therein, proximal to the coding region or exons of a gene of interest, a regulatory or amplifying segment which does not naturally appear thereat.

It is another object of the present invention to provide DNA constructs which can be used for accomplishing the homologous recombination methods of the present invention.

It is a further object of the present invention to provide cell lines and microorganisms which include the genomes in accordance with the present invention.

These and other objects of the present invention are accomplished by means of the technique of homologous recombination, by which one of ordinary skill in this art can cause the expression and, preferably, amplification of resident, albeit transcriptionally silent genes. By this technique, one can also modify the expression characteristics of a gene which is naturally present, but not necessarily silent or inert, within the genome of a stable cell line, such as, for example, to make the expression conditional, i.e., repressible or inducible, or to enhance the rate of expression.

The present invention provides a method of modifying the expression characteristics of a gene within the genome of a cell line or microorganism. A DNA construct is inserted into that genome by the technique of homologous recombination. The construct includes a DNA regulatory segment capable of modifying the expression characteristics of any gene to which it is operatively linked within the host cell line or microorganism, as well as a targeting segment homologous to a region of the genome at which it is desired for the DNA regulatory segment to be inserted. The construct and insertion technique is designed to cause the new DNA regulatory segment to be operatively linked to the gene of interest. Thus, without necessarily inserting any new coding exons, the expression characteristics of that gene are modified. In the preferred embodiment, the gene is one which is normally transcriptionally silent or inert within the host cell line or microorganism and, by means of the DNA regulatory region, which is targeted directly to the appropriate position with respect to that gene by means of homologous recombination, that gene is thereby activated for expression of its gene product.

The DNA construct preferably includes two targeting segments which, while separated from one another in the construct by those elements to be inserted into the genome, are preferably contiguous in the native gene.

The construct further preferably includes at least one expressible selectable marker gene, such as the gene providing neomycin resistance. This marker gene, including a promoter therefor, is also disposed between the two targeting regions of the construct.

In another embodiment, the construct includes an expressible amplifiable gene in order to amplify expression of the gene of interest. This gene, including a promoter therefor, is also disposed between the two targeting regions of the construct. In some cases the selectable marker and the amplifiable marker may be the same.

In a further embodiment of the present invention, the DNA construct includes a negative selectable marker gene which is not expressed in cells in which the DNA construct is properly inserted. This negative selectable marker gene is disposed outside of the two targeting regions so as to be removed when the construct is properly combined into the gene by homologous recombination. An example of such a negative selectable marker gene is the Herpes Simplex Virus thymidine kinase gene.

In yet a further embodiment, it is possible to modify the expression characteristics of a specific gene which already expresses a product in the cell line or microorganism of interest. This can be accomplished by inserting by homologous recombination a DNA construct which includes (1) an expressible amplifiable gene which increases the copy number of the gene of interest when the cell line or microorganism is subjected to amplification conditions and/or (2) a promoter/enhancer element (or other regulatory element) which modifies the expression of the gene of interest such as, for example, by increasing the rate of transcription, increasing translation efficiency, increasing mRNA accumulation, making the expression inducible, etc. The gene expression which is modified in this manner may be natural expression or expression which has been caused by previous genetic manipulation of the cell line or microorganism. The previous genetic manipulation may have been by conventional techniques or by means of homologous recombination in accordance with the present invention. In the latter case, the DNA insertion which results in the modification of expression characteristics may be accomplished as part of the same genetic manipulation which results in expression of the gene or may be performed as a subsequent step.

The present invention also includes the constructs prepared in accordance with the above discussion as well as the genomes which have been properly subjected to homologous recombination by means of such constructs and the cell lines and microorganisms including these genomes. Moreover, a process for preparation of the desired product by culturing the transformed cells according to the present invention is also included.

BRIEF DESCRIPTION OF THE DRAWINGS

FIG. 2A shows the mode of integration of the DNA construct into the genome in the event of non-homologous or random recombination.

FIG. 2B shows the mode of integration of the DNA construct in the genome in the event of homologous recombination.

FIG. 5 shows the pRSVCAT plasmid, including the restriction sites thereof.

FIG. 7 shows the pSV2NEO plasmid, including the restriction sites thereof.

FIG. 9 shows the construction of the pRSVNEO plasmid, including the restriction sites thereof.

FIG. 14 shows a portion of the nucleotide sequence of TSHB along with the regions thereof to which each primer for PCR amplification corresponds. Exons 2 and 3 are shown in capital letters. A 247 BP amplified fragment is shown by underlined asterisks.

FIG. 14 shows the results of polyacrylamide gel electrophoresis of cDNA synthesized from RNA extracted from various cell populations and whose TSHB cDNA, if present, has been amplified by PCR. The nature of the cells representing the various lanes is set forth in FIG. 15 below the gel.

DETAILED DESCRIPTION OF PREFERRED EMBODIMENTS

Figure 1:
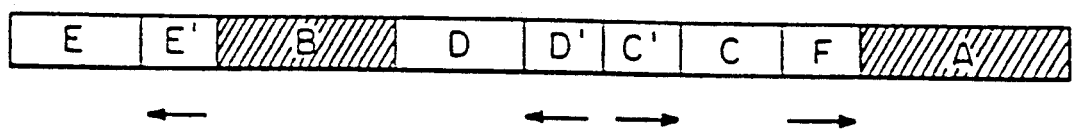
FIG. 1 shows a general outline of a DNA construct in accordance with the present invention.

Homologous recombination is a technique developed within the past few years for targeting genes to induce or correct mutations in transcriptionally active genes (Kucherlapati, *Prog. in Nucl. Acid Res. and Mol. Biol.*, 36:301 (1989)). This technique of homologous recombination was developed as a method for introduction of specific mutations into specific regions of the mammalian genome (Thomas et al., *Cell*, 44:419-428, 1986; Thomas and Capecchi, *Cell*, 51:503-512, 1987; Doetschman et al., *Proc. Natl. Acad. Sci.* 85:8583-8587, 1988) or to correct specific mutations within defective genes (Doetschman et al., *Nature*, 330:576-578, 1987).

Through this technique, a piece of DNA that one desires to be inserted into the genome can be directed to a specific region of the gene of interest by attaching it to "targeting DNA". "Targeting DNA" is DNA that is complementary (homologous) to a region of the genomic DNA. If two homologous pieces of single stranded DNA (i.e., the targeting DNA and the genomic DNA) are in close proximity, they will hybridize to form a double stranded helix. Attached to the targeting DNA is the DNA sequence that one desires to insert into the genome.

There are a number of methods by which homologous recombination can occur. One example is during the process of replication or DNA during mitosis in cells.

Through a mechanism that is not completely understood, parental double-stranded DNA is opened immediately prior to cell division at a local region called the replication bubble. The two separated strands of DNA may now serve as templates from which new strands of DNA are synthesized. One arm of the replication fork has the DNA code in the 5' to 3' direction, which is the appropriate orientation from which the enzyme DNA polymerase can "read". This enzyme attaches to the 5' portion of the single stranded DNA and using the strand as a template, begins to synthesize the complementary DNA strand. The other parental strand of DNA is encoded in the 3' to 5' direction. It cannot be read in this direction by DNA polymerase. For this strand of DNA to replicate, a special mechanism most occur.

A specialized enzyme, RNA primase, attaches itself to the 3' to 5' strand of DNA and synthesizes a short RNA primer at intervals along the strand. Using these RNA segments as primers, the DNA polymerase now attaches to the primed DNA and synthesizes a complementary piece of DNA in the 5' to 3' direction. These pieces of newly synthesized DNA are called Okazaki fragments. The RNA primers that were responsible for starting the entire reaction are removed by the exonuclease function of the DNA polymerase and replaced with DNA. This phenomenon continues until the polmmerase reaches an unprimed stretch of DNA, where the local synthetic process stops. Thus, although the complementary parental strand is synthesized overall in the 3' to 5' direction, it is actually produced by "backstitching" in the 5' to 3' direction. Any nicks that might occur in the DNA during the "backstitching" process are sealed by an enzyme called DNA ligase.

To maintain an absolute fidelity of the DNA code, a proofreading function is present within the DNA polymerase. The DNA polymerase requires primed pieces of DNA upon which to synthesize a new strand of DNA. As mentioned above, this can be a single strand of DNA primed with RNA, or a complementary strand of DNA. When the DNA polymerase finds mismatched complementary pieces of DNA, it can act as an exonuclease and remove DNA bases in a 3' to 5' direction until it reaches perfect matching again.

With this background, it is now possible to understand the basis of the technique described herein. Small pieces of targeting DNA that are complementary to a specific region of the genome are put in contact with the parental strand during the DNA replication process. It is a general property of DNA that has been inserted into a cell to hybridize and therefore recombine with other pieces of DNA through shared homologous regions. If this complementary strand is attached to an oligonucleotide that contains a mutation or a different sequence of DNA, it too is incorporated into the newly synthesized strand as a result of the recombination. As a result of the proofreading function, it is possible for the new sequence of DNA to serve as the template. Thus, the transfected DNA is incorporated into the genome.

If the sequence of a particular gene is known, a piece of DNA that is complementary to a selected region of the gene can be synthesized or otherwise obtained, such as by appropriate restriction of the native DNA at specific recognition sites bounding the region of interest. This piece will act as a targeting device upon insertion into the cell and will hybridize to its homologous region within the genome. If this hybridization occurs during DNA replication, this piece of DNA, and any additional sequence attached thereto, will act as an Okazaki fragment and will be backstitched into the newly synthesized daughter strand of DNA.

In the technique of the present invention, attached to these pieces of targeting DNA are regions of DNA that are known to interact with the nuclear regulatory proteins present within the cell and, optionally, amplifiable and selectable DNA markers. Thus, the expression of specific proteins may be achieved not by transfection of DNA that encodes the gene itself and marker DNA, as is most common, but rather by the use of targeting DNA (regions of homology with the endogenous gene of interest) coupled with DNA regulatory segments that provide the gene with recognizable signals for transcription. With this technology, it is possible to express and to amplify any cognate gene present within a cell type without actually transfecting that gene. In addition, the expression of this gene is controlled by the entire genomic DNA rather than portions of the gene or the cDNA, thus improving the rate of transcription and efficiency of mRNA processing. Furthermore, the expression characteristics of any cognate gene present within a cell type can be modified by appropriate insertion of DNA regulatory segments and without inserting entire coding portions of the gene of interest.

In accordance with these aspects of the instant invention there are provided new methods for expressing normally transcriptionally silent genes of interest, or for modifying the expression of endogenously expressing genes of interest, within a differentiated cell line. The cognate genomic sequences that are desired to be expressed, or to have their expression modified, will be provided with the necessary cell specific DNA sequences (regulatory and/or amplification segments) to direct or modify expression of the gene within the cell. The resulting DNA will comprise the DNA sequence coding for the desired protein directly linked in an operative way to heterologous (for the cognate DNA sequence) regulatory and/or amplification segments. A positive selectable marker is optionally included within the construction to facilitate the screening of resultant cells. The use of the neomycin resistance gene is preferred, although any selectable marker may be employed. Negative selectable markers may, optionally, also be employed. For instance, the Herpes Simplex Virus thymidine kinase (HSVtk) gene may be used as a marker to select against randomly integrated vector DNA. The fused DNAs, or existing expressing DNAs, can be amplified if the targeting DNA is linked to an amplifiable marker.

Therefore, in accordance with the method of the present invention, any gene which is normally expressed when present in its specific eukaryotic cell line, particularly a differentiated cell line, can be forced to expression in a cell line not specific for it wherein the gene is in a silent format. This occurs without actually inserting the full DNA sequence for that gene. In addition, that gene, or a normally expressing gene, can be amplified for enhanced expression rates. Furthermore, the expression characteristics of genes not totally transcriptionally silent can be modified as can the expression characteristics of genes in microorganisms.

In one embodiment of the present invention, eukaryotic cells that contain but do not normally transcribe a specific gene of interest are induced to do so by the technique described herein. The homologous recombination vector described below is inserted into a clonal cell line and, following chemical selection, is monitored for production of a specific gene product by any appropriate means, such as, for example, by detection of mRNA transcribed from the newly activated gene, immunological detection of the specific gene product, or functional assay for the specific gene product.

The general outline of the DNA construct that is used to transcriptionally activate endogenous genes by homologous recombination is depicted in FIG. 1.

In general, the DNA construct comprises at least two and up to six or more separate DNA segments. The segments consist of at least one, preferably two, DNA targeting segments (A and B) homologous to a region of the cell genome within or proximal to the gene desired to be expressed, a positive selection gene (C), an amplifiable gene (D), a negative selection gene (E) and a DNA regulatory segment (F) which is transcriptionally active in the cell to be transfected. In the most basic embodiment of the present invention, only a single targeting segment (B) and the regulatory segment (F) must be present. All of the other regions are optional and produce preferred constructs.

Regions A and B are DNA sequences which are homologous to regions of the endogenous gene of interest which is to be made transcriptionally active. The specific regions A and B of the endogenous gene are selected so as to be upstream and downstream, respectively, of the specific position at which it is desired for the regulatory segment to be inserted. Although these regions are separated in the construct they are preferably continuous in the endogenous gene. There may be occasions where non-contiguous portions of the genome are utilized as targeting segments, for example, where it is desired to delete a portion of the genome, such as a negative regulatory element.

Figure 4:
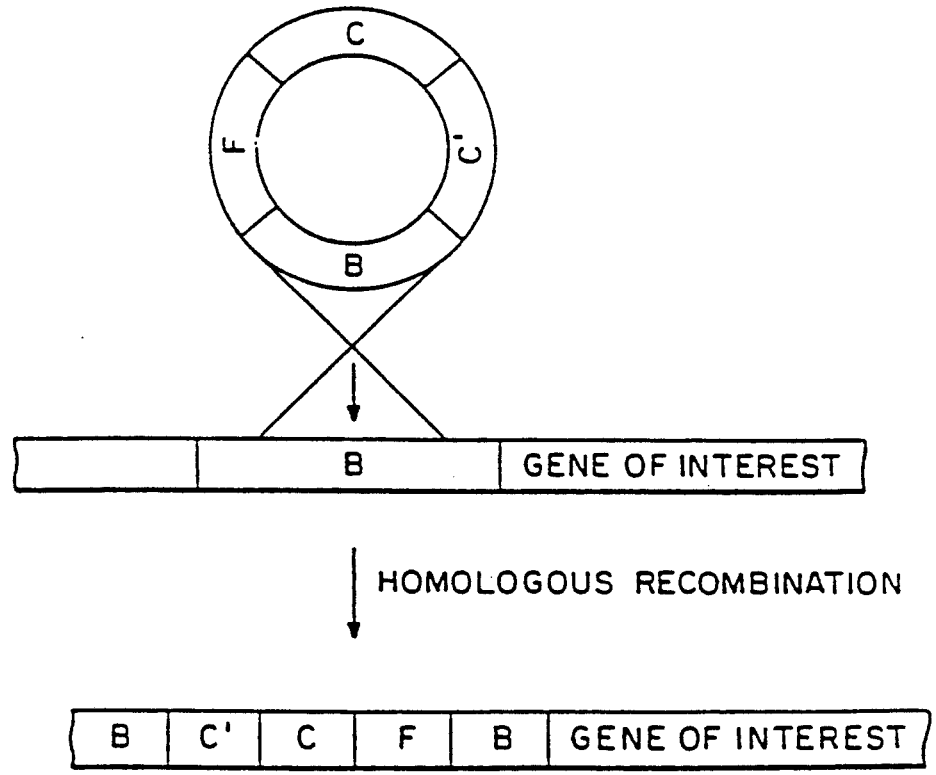
FIG. 4 shows the mode of integration of a circular piece of DNA by homologous recombination when only a single targeting piece of DNA is employed.

While two targeting regions, A and B, are preferred in order to increase the total regions of homology and thus increase recombination efficiency, the process of the present invention also comprehends the use of only a single targeting region. In its simplest form (when only the regulatory segment F and the selectable marker gene C and promoter C' are to be inserted), a circular piece of DNA is employed which contains these elements along with the targeting DNA (see FIG. 4). In this way, the homologous region (B) hybridizes with its genomic counterpart. Segments C', C and F are inserted within the B portion of the cognate gene following the crossover event.

When it is desired for the DNA regulatory sequence to be inserted upstream of the gene of interest, as, for example, when it is desired to activate and express a normally transcriptionally silent gene, the region of homology is preferably homologous to a non-coding portion of the genome upstream of the coding portions of the gene of interest. When two targeting regions are present, the downstream region (A) may include a portion of the coding region, although it is preferred that it, too, be totally upstream of the coding region. It is further preferred that the homologous regions be chosen such that the DNA regulatory sequence will be inserted downstream of the native promoter for the gene of interest, particularly if the native promoter is a negative promoter rather than a turned-off positive promoter.

The size of the targeting regions, i.e., the regions of homology, is not critical, although the shorter the regions the less likely that they will find the appropriate regions of homology and recombine at the desired spot. Thus, the shorter the regions of homology, the less efficient is the homologous recombination, i.e., the smaller the percentage of successfully recombined clones. It has been suggested that the minimum requirement for sequence homology is 25 base pairs (Ayares et al, *PNAS, USA* 83:5199-5203, 1986). Furthermore, if any of the other elements of the construct are also found in the genome of the host cell, there is a possibility of recombination at the wrong place. However, in view of the excellent positive and negative selectability of the present invention, it can be successfully practiced even if the efficiency is low. The optimum results are achieved when the total region of homology, including both targeting regions is large, for example one to three kilobases. As long as the regulatable segment F can be operatively linked to the gene of interest there is no limit to the size of the targeting region, and particularly the upstream targeting region B.

It can easily be empirically determined whether or not the targeting regions are too large or the regulatable segment F spaced too far from the coding region of the gene to be operatively linked thereto. In such a case, the regions A and B can be made homologous to a different section of the gene of interest and the process repeated until the regulatable segment F is properly inserted so as to be operatively linked to the gene of interest. For example, the restriction site of combined region A-B of the endogenous gene can be changed and the process repeated. Once the concept of the present invention is known, along with the techniques disclosed herein, one of ordinary skill in this art would be able to make and use the present invention with respect to any given gene of interest in any cell line or microorganism without use of undue experimentation.

Region C is a positive selectable marker gene which is capable of rendering the transfected cell line resistant to a normally toxic environment. Examples of such genes are adenosine deaminase (ADA), aminoglycoside phosphotransferase (neo), dihydrofolate reductase (DHFR), hygromycin-B-phosphotransferase (HPH), thymidine kinase (tk), xanthine-guanine phosphoribosyltransferase (gpt), multiple drug resistance gene (MDR), ornithine decarboxylase (ODC) and N-(phosphonacetyl)-L-aspartate resistance (CAD).

In addition to the positive selectable marker gene, an amplifiable gene is also optionally included in the construct at region D. Amplifiable genes are genes that lead to an increase in copy number when under selective pressure. The copy number of a gene positioned adjacent to the amplifiable gene will also increase. Amplifiable genes that can be utilized include DHFR, MDR, ODC, ADA and CAD. The members of the positive selectable marker gene group and those of the amplifiable gene group overlap so that, in theory, instead of using two genes, one for positive selection and one for amplification, one gene could be used for both purposes. However, since most cell lines contain endogenous copies of these amplifiable genes, the cells will already be somewhat resistant to the selection conditions and distinguishing the cells which have transfected DNA from those which do not receive transfected DNA can be difficult. Thus, in instances where an amplifiable gene is desired, a positive selection gene which is dominant, such as HPH, gpt, neo and tk (in tk-cells), should also be included in the construct. For some applications it may be possible or preferable to omit the amplifiable marker. For instance, the gene of interest may not need to be amplified as, for example, when transcriptional activation by the heterologous DNA regulatory sequence is sufficient without amplification. Also, if the homologous recombination efficiency is very low, it may be necessary to leave out the amplifiable gene since the ratio of non-homologous DNA to homologous DNA is directly related to the homologous recombination efficiency (Letsou, *Genetics.* 117:759-770, 1987). It is also possible to eliminate the positive selection gene and select cells solely by screening for the production of the desired protein or mRNA. However, it is preferred in most cases to include at least the positive selection gene.

Region E of the construct is a negative selectable marker gene. Such a gene is not expressed in cells in which the DNA construct is properly inserted by homologous recombination, but is expressed in cells in which the DNA construct is inserted improperly, such as by random integration. One such gene is the Herpes Simplex Virus thymidine kinase gene (HSVtk). The HSVtk has a lower stringency for nucleotides and is able to phosphorylate nucleotide analogs that normal mammalian cells are unable to phosphorylate. If the HSVtk is present in the cells, nucleotide analogs such as acyclovir and gancyclovir are phosphorylated and incorporated into the DNA of the host cell thus killing the cell. The presence of the negative selectable marker gene enables one to use the positive-negative selection for homologous recombination as described by Mansour et al (*Nature,* 336:348-352, 1988). Capecchi uses a strategy which takes advantage of the differing modes of integration that occur when linearized vector DNA inserts via homologous recombination as compared to when it inserts by random integration. If the vector DNA inserts randomly, the majority of the inserts will insert via the ends (Folger et al, *Mol. Cell. Biol.,* 2:1372-1387, 1982; Roth et al., *Mol. Cell. Biol.,* 5:2599-2607, 1985; and Thomas et al, *Cell,* 44:419-428, 1986). On the other hand, if the vector inserts by homologous recombination, it will recombine through the regions of homology which cause the loss of sequences outside of those regions.

Using the construct depicted in FIG. 1 as an example, the mode of integration for homologous recombination versus random integration is illustrated in FIGS. 2A and 2B. In the case of non-homologous recombination (FIG. 2A), the vector is inserted via the ends of the construct. This allows region E, in this case the HSVtk gene, to be inserted into the genome. However, when homologous recombination occurs (FIG. 2B), the HSVtk gene is lost. The first round of selection uses the appropriate drug or conditions for the positive selection present within the construct. Cells which have DNA integrated either by homologous recombination or random integration will survive this round of selection. The surviving cells are then exposed to a drug such as gancyclovir which will kill all the cells that contain the HSVtk gene. In this case, most of the cells in which the vector integrated via a random insertion contain the HSVtk gene and are killed by the drug while those in which the vector integrated by homologous recombination have lost the HSVtk gene and survive. This allows the elimination of most of the cells which contain randomly integrated DNA, leaving the majority of the surviving cells containing DNA which integrated via homologous recombination. This greatly facilitates identification of the correct recombination event.

The negative selection step can also be eliminated if necessary. It will require that the screening step be more labor intensive involving the need for techniques such as polymerase chain reaction (PCR) or immunological screening.

The sixth region (F) contains the DNA regulatory segment that will be used to make the gene of interest transcriptionally active. The appropriate DNA regulatory segment is selected depending upon the cell type to be used. The regulatory segment preferably used is one which is known to promote expression of a given gene in differentiated host cell line. For example, if the host cell line consists of pituitary cells which naturally express proteins such as growth hormone and prolactin, the promoter for either of these genes can be used as DNA regulatory element F. When inserted in accordance with the present invention, the regulatory segment will be operatively linked to the normally transcriptionally silent gene of interest and will stimulate the transcription and/or expression of that gene in the host cell line. Also usable are promiscuous DNA regulatory segments that work across cell types, such as the rous sarcoma virus (RSV) promoter. As long as the regulatory segment stimulates transcription and/or expression, or can be induced to stimulate transcription and/or expression, of the gene of interest after being inserted into the host cell line so as to be operatively linked to the gene of interest by means of the present invention, it can be used in the present invention. It is important when joining the regulatory segment F to the targeting segment A that no starting codon be accidentally introduced into the sequence since such an occurrence could alter the reading frame of the gene which is desired to be expressed. Of course, the construct must be constructed and inserted such that the regulatory segment F is operatively linked to the gene of interest.

The DNA regulatory segment, region F, need not be present in instances where it is desired to enhance or amplify the transcription of a gene which is already expressing in the cell line of interest, either because it naturally expresses in that cell line or because the cell line has previously had its DNA manipulated to cause such expression. In such instances, insertion of an amplifiable gene, region D, preferably with the positive selectable marker gene, region C, and optionally also with a negative selectable marker gene, region E, will be sufficient to increase the copy number of the gene of interest and thus enhance the overall amount of transcription. Alternatively, a new regulatory segment, region F, inherently promoting an increased (or otherwise modified) rate of transcription as compared to the existing regulatory region for the gene of interest, may be included to further enhance the transcription of the existing expressing gene of interest. Such a new regulatory segment could include promoters or enhancers which improve transcription efficiency.

Regions C', D' and E' are promoter regions which are used to drive the genes in regions C, D, and E, respectively. These promoters are transcriptionally active in the cell line chosen and may be the same or different from the promoter in region F used to drive the endogenous gene of interest. The specific direction of transcription specified in FIG. 1 is not critical. Those of ordinary skill in this art can determine any appropriate placement of the genes C, D and E and their promoters C', D' and E' such that the promoters will stimulate expression of their associated genes without simultaneously disrupting in any way the expression of the gene of interest or any of the other genes of the construct.

The present invention may be illustrated by reference to the activation of the rat thyrotropin beta subunit (TSH$\beta$) in GH (ATCC CCL 82), GH$_3$ (ATCC CCL 82.1) or GH$_4$Cl cell lines (GH). GH cell lines are derived from a radiation induced pituitary tumor in rats designated MtT/W5 (Takemoto, *Cancer Res.*, 22:917, 1962) and adapted to grow in culture by Tashjian et al, *Endocrinology*, 82:342-352, 1968. These cell lines may be subcloned and screened for their ability to produce growth hormone and TSH$\beta$. Such screening may preferably be by means of Northern blot analysis to determine whether mRNA for the rat growth hormone gene is present and to establish that there is no mRNA for the TSH$\beta$ gene being produced. The cell lines may also be screened by Southern analysis to determine that there is at least one copy of the TSH$\beta$ gene present within the genome. Only the GH cell lines that produce growth hormone and not TSH$\beta$, but contain a copy of the TSH$\beta$ gene, are used.

Figure 3:
FIG. 3 shows the construction of a preferred homologous recombination vector in accordance with the present invention.

The specific homologous recombination vector for use in GH cells may be designed in the following manner (FIG. 3). Region A may consist of the 5' upstream untranslated region of the TSH$\beta$ gene defined by the HindIII fragment which stretches from $-74$ to $-2785$ and region B may contain the DNA fragment that stretches from the $-2785$ HindIII site to a NcoI site approximately 2.1 kb further upstream as described by Carr et al (*J. Biol. Chem.*, 262:981-987, 1987) and Croyle et al (*DNA*, 5:299-304, 1986). The positive selection gene (region C) may be a 1067 bp BglII-SmaI fragment derived from the plasmid pSV2neo (ATCC No. 37, 149) (Southern et al, *J. Mol. Appl. Gen.*, 1:327-341, 1982). The neo gene may be driven by the Rous Sarcoma Virus (RSV) promoter (region C') which is derived from the NdeI-HindIII fragment from the plasmid pRSVcat (ATCC No. 37, 152) (Gorman et al, *PNAS.* 79:6777-6781, 1982). In this example, no amplifiable marker need be used and thus there need be no region D in order to optimize the efficiency of the homologous recombination. The efficiency is inversely related to the proportion of non-homologous to homologous sequences present in the construct (Letsou et al, *Genetics,* 117:759-770, 1987). Region E, or the negative selection gene, may consist of the HSVtk gene which is a 2 kb Xho fragment obtained from the plasmid pMCITK (Capecchi et al, *Nature,* 336:348-352, 1988). The HSVtk gene in that construct may be driven by the polyoma virus promoter and enhancer (region E') as constructed by Thomas et al (*Cell,* 51:503-512, 1987). In a second DNA construct the polyoma promoter may be replaced by the RSV promoter described above. The DNA regulatory sequence used to activate the TSH$\beta$ gene may be either the RSV promoter or the rat growth hormone promoter. The rat growth hormone promoter consists of the SacI-EcoRI fragment obtained from the plasmid pRGH237CAT (Larson et al, pNAS, 83:8283-8287, 1986). The RSV promoter has the advantage of being usable in other cell lines besides GH cells, while the GH promoter is known to be active in GH cells and can be specifically induced (Brent et al, *J. Biol. Chem.*, 264:178-182, 1989). The rat growth hormone promoter and the RSV promoter may be inserted at location F in separate constructs.

Following transfection of the above construct into a GH cell line, the cells may be grown in media that contains G418. This will allow only those cells which have integrated plasmid DNA into the genome either by homologous recombination or random integration to grow. The surviving cells may be grown in media that contains gancyclovir. The majority of the cells that survive this round of selection will be those in which the vector plasmid DNA is integrated via homologous recombination. These cells may be screened to demonstrate that they are producing mRNA which corresponds to the TSH$\beta$ gene and that they are producing the TSH$\beta$ protein. The genomic DNA may also be sequenced around the area of insertion of the heterologous promoter to insure that the proper recombination event occurred.

EXAMPLE—ACTIVATION OF TSH$\beta$ GENE IN RATE PITUITARY CELLS

Using the following protocol, thyrotropin beta subunit (TSH$\beta$) gene transcription, which normally does not occur in the rat GH$_3$ pituitary cell line, was activated in those cells by using the process of homologous recombination to target an activating element upstream of the TSH$\beta$ coding region. The Rous Sarcoma Virus (RSV) promoter is known to function efficiently in GH3 cells (Christian Nelson et al, *Nature.* 322:557-562 (1986); Zheng-Sheng Ye et al, *The Journal of Biological Chemistry,* 263:7821-7829 (1988)) and therefore was chosen as the activating element. A plasmid vector was constructed which contained the RSV activating element, portions of the 5' flanking region of the TSH$\beta$ gene locus, and a selectable drug marker, aminoglycoside phosphotransferase gene (NEO), for the isolation of transfected cell populations. Ribonucleic acid (RNA) was extracted from pooled drug resistant GH$_3$ cell populations and converted to complementary deoxyribonucleic acid (cDNA). The cDNA was then screened by the technique of polymerase chain reaction (PCR) for the presence of TSR$\beta$ cDNA. The constuction of the homologous recombination vectors and the control vectors is outlined below along with the experimental procedures and results.

PLASMID CONSTRUCTION

Homologous Recombination (HR) Backbone Vector (oRSVCATNEO)

Figure 6:
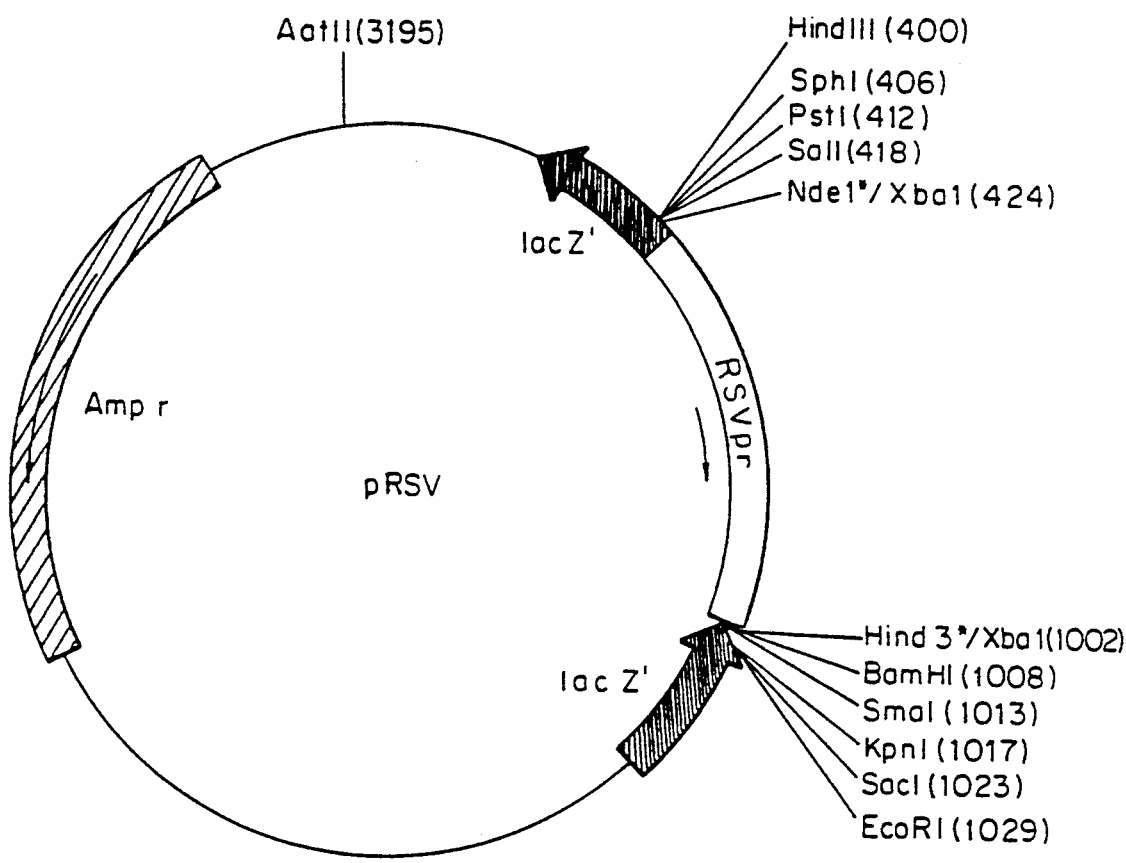
FIG. 6 shows the construction of the pRSV plasmid, including the restriction sites thereof.
Figure 8:
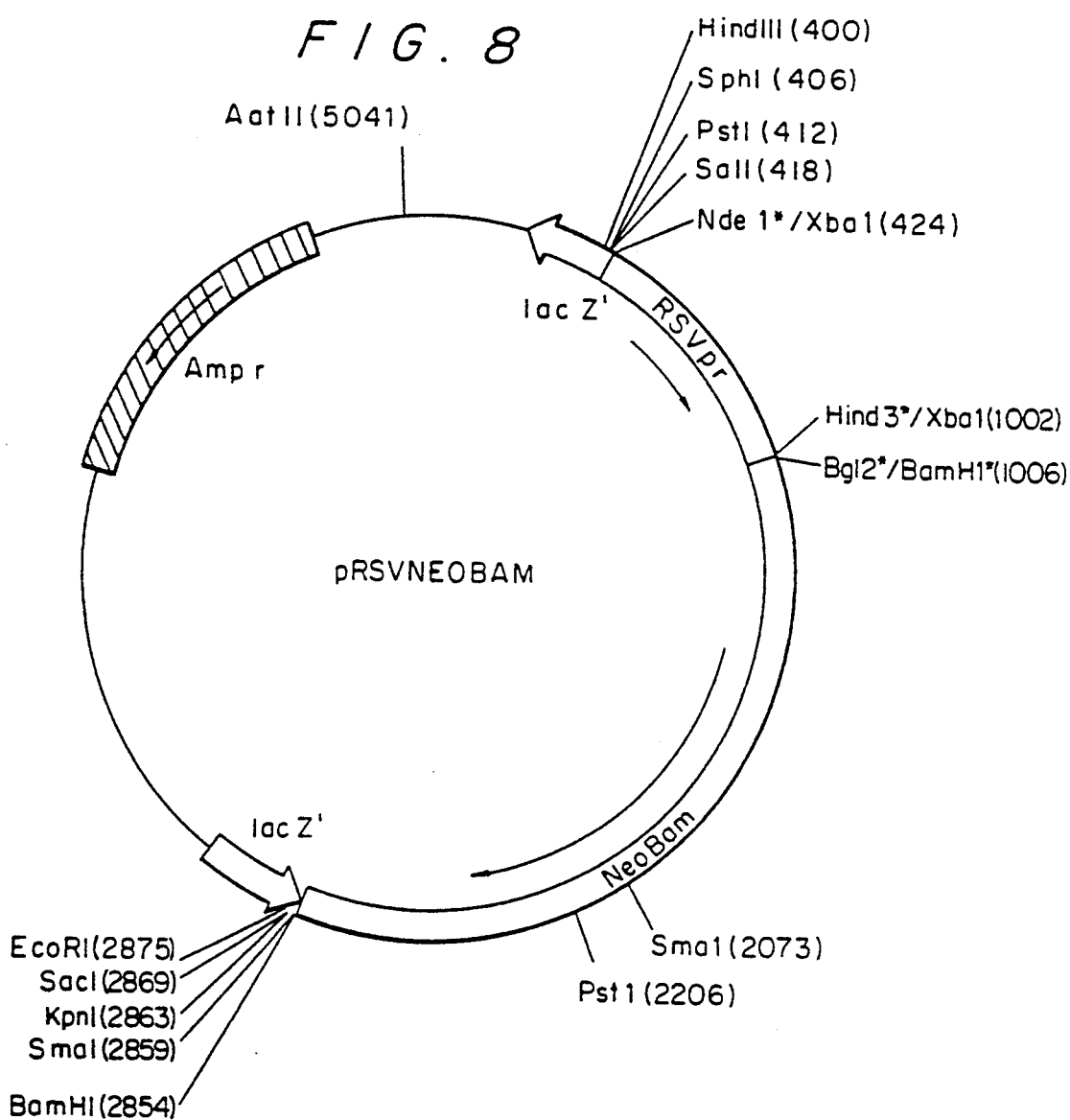
FIG. 8 shows the construction of the pSVNEOBAM plasmid, including the restriction sites thereof.

The Rous Sarcoma Virus (RSV) promoter was derived from the plasmid pRSVCAT (Cornelia M. Gorman et al., *Proceedings of the National Academy of Science,* 79:6777-6781 (1982)) (FIG. 5) by isolating the 580 base pair (bp) NdeI - HindIII fragment containing the functional promoter unit. The ends of this fragment were blunted using DNA polymerase I Klenow fragment and XbaI linkers ligated to the blunt ends. After digestion with XbaI restriction endonuclease and gel purification, the resulting fragment was ligated into the XbaI site of pUC18. A bacterial colony harboring a plasmid with the RSV insert in the orientation shown in FIG. 6 was designated pRSV. The aminoglycoside phosphotransferase gene (NEO) was cloned from pSV2NEO (P. J. Southern et al., *Journal of Molecular and Applied Genetics.* 1:327-341 (1982)) by isolating the BglII and BamHI fragment (FIG. 7) and ligating that fragment into the BamHI site of pRSV (FIG. 6). A plasmid containing the NEO gene in the orientation shown in FIG. 8 was picked and designated pRSVNEOBAM. pRSVNEOBAM was digested with SmaI and the 4328 bp fragment containing the RSV promoter region, the majority of the NEO gene and pUC18 was isolated by gel electrophoresis. The SmaI ends of this fragment were XhoI linkered, cleaved with XhoI restriction enzyme and the plasmid recircularized by ligation. The resulting plasmid is shown in FIG. 9 and is called pRSVNEO. This last cloning step resulted in the deletion of a 786 bp fragment from the 3' end of the NEO fragment which is not necessary for its functional expression. This construction yields a plasmid in which the NEO gene is transcriptionally driven by the RSV promoter.

Figure 10:
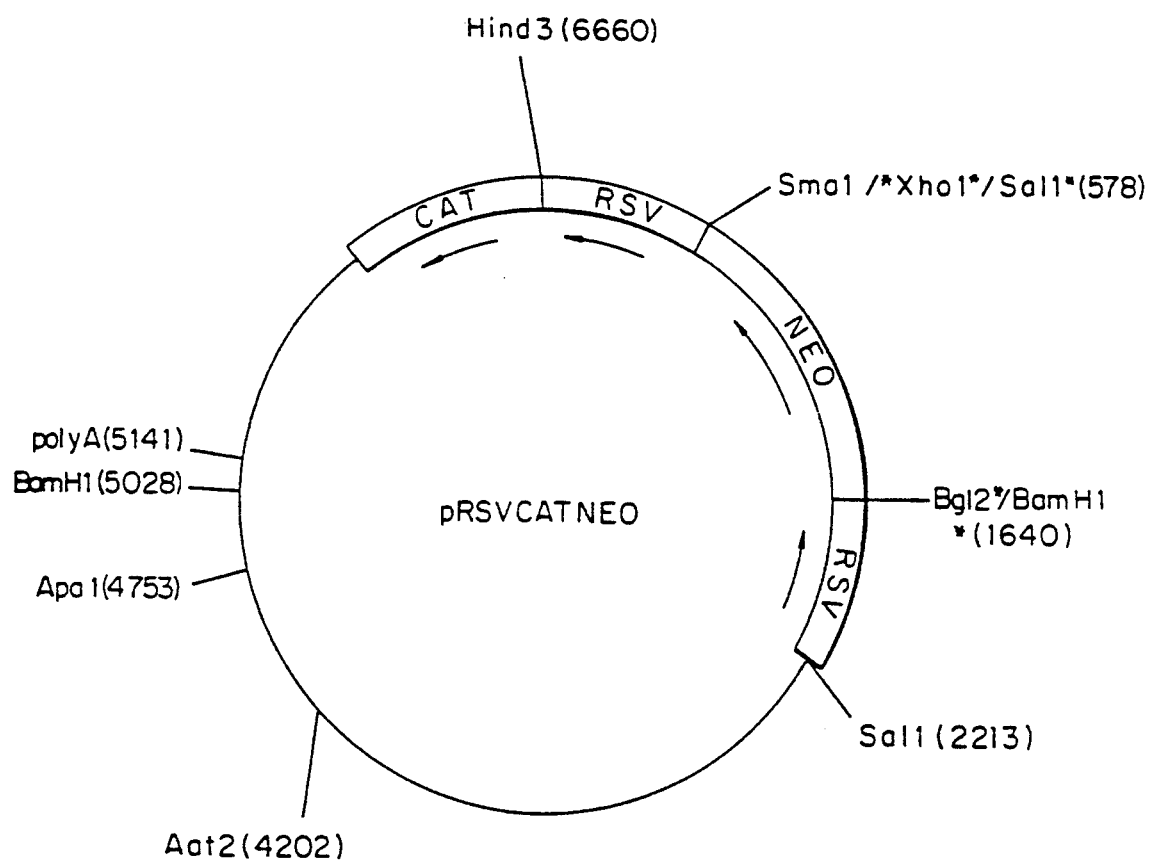
FIG. 10 shows the construction of the pRSVCATNEO plasmid, including the restriction sites thereof.

Next the NdeI site located 5' of the RSV promoter in pRSVCAT (FIG. 5) was converted to a SalI site. This was accomplished by digesting pRSVCAT with NdeI, filling in the ends using DNA polymerase I Klenow fragment and ligating SalI linkers to the resulting blunt ends. The linkers were digested to completion with SalI and the plasmid recircularized by ligation. Into the newly constructed SalI site was cloned the SalI - XhoI fragment from pRSVNEO (FIG. 9) containing the RSV promoter and the NEO gene. A plasmid with the RSV promoter and NEO fragment oriented as shown in FIG. 10 was isolated and named pRSVCATNEO. This plasmid when transfected into GH$_3$ cells was capable of conferring G418 resistance to those cells, demonstrating the ability of the RSV promoter to drive transcription of the NEO gene and the ability of that RNA to be translated into a functional protein (data not shown). Total RNA from the stable transfectants above was analyzed by polymerase chain reaction (PCR) to determine whether the CAT gene was being transcribed. PCR results showed that the CAT gene was indeed being transcribed in all the G418 resistant colonies tested (data not shown), indicating that the RSV promoter 5' of the CAT gene was capable of driving transcription of a gene located 3' to it. This is important because this RSV promoter will be responsible for driving transcription of the TSH$\beta$ gene when the TSH$\beta$ HR vector described below integrates via homologous recombination into the GB$_3$ genome.

TSH$\beta$ HR VECTOR

Figure 11:
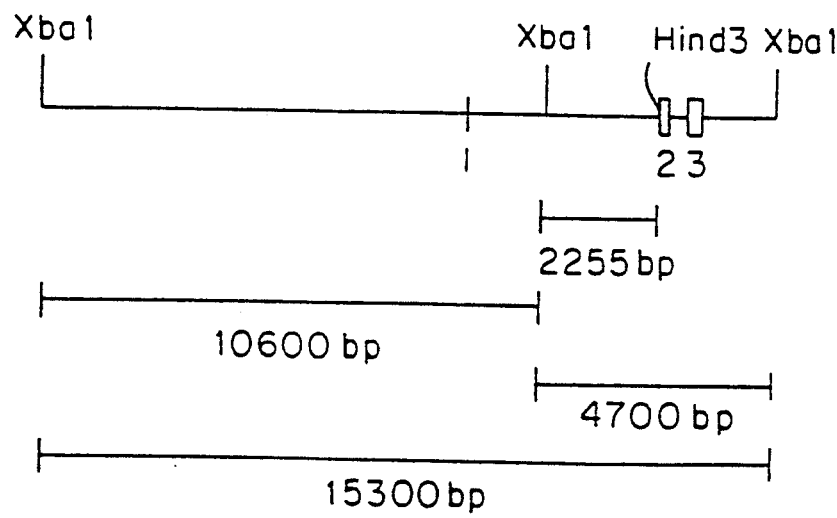
FIG. 11 shows a 15.3 kb fragment of the rat TSHB gene and showing various restriction segments thereof.
Figure 12:
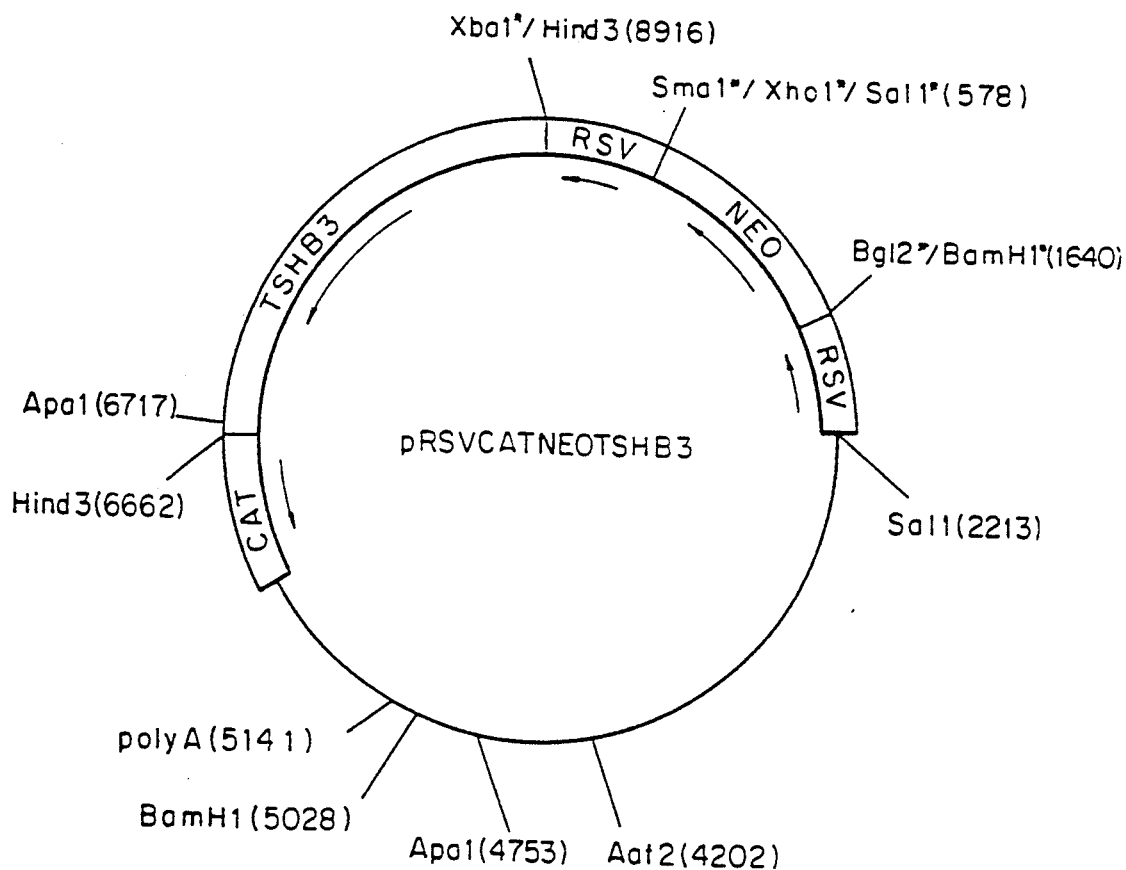
FIG. 12 shows the construction of the pRSVCAT-NEOTSHB3 plasmid, including the restriction sites thereof.

A vector capable of integrating into the GH$_3$ genome by homologous recombination was created by inserting two stretches of the 5' flanking regions of the thyrotropin beta subunit (TSH$\beta$) gene into the unique SalI and HindIII sites contained in pRSVCATNEO (FIG. 10). A rat spleen genomic library containing inserts of 15 kilobases (kb) or greater cloned into lambda DASH was obtained from Stratagene, San Diego, Calif. Using standard protocols (*Current Protocols in Molecular Biology*, pp. 1.9.1–1.13.6, 6.1.1–6.4.10) a 15 3 kb clone of the rat genomic TSH$\beta$ gene including 9kb of sequence 5' of the first exon was isolated The 15.3 kb fragment consisted of two XbaI fragments, a 10.6 kb fragment corresponding to the 5' end of the 15.3 kb fragment and a 4.7 kb piece corresponding to the 3' region of the 15.3 kb fragment (FIG. 11). Both of these XbaI fragments were subcloned into pUC18 and plasmids containing inserts in both orientations were isolated. The 2.3 kb XbaI - HindIII fragment contained in the 4.7 kb XbaI fragment (figure il) was purified and the XbaI site of this fragment was converted to a HindIII site by filling in the ends with Klenow fragment and ligating on HindIII linkers. This fragment was ligated into the unique HindIII site contained in pRSVCATNEO (FIG. 10). An isolate corresponding to a plasmid with the 2.3 kb insert in the correct orientation as shown in FIG. 12 was assigned the name pRSVCATNEOTSHB3.

Figure 13:
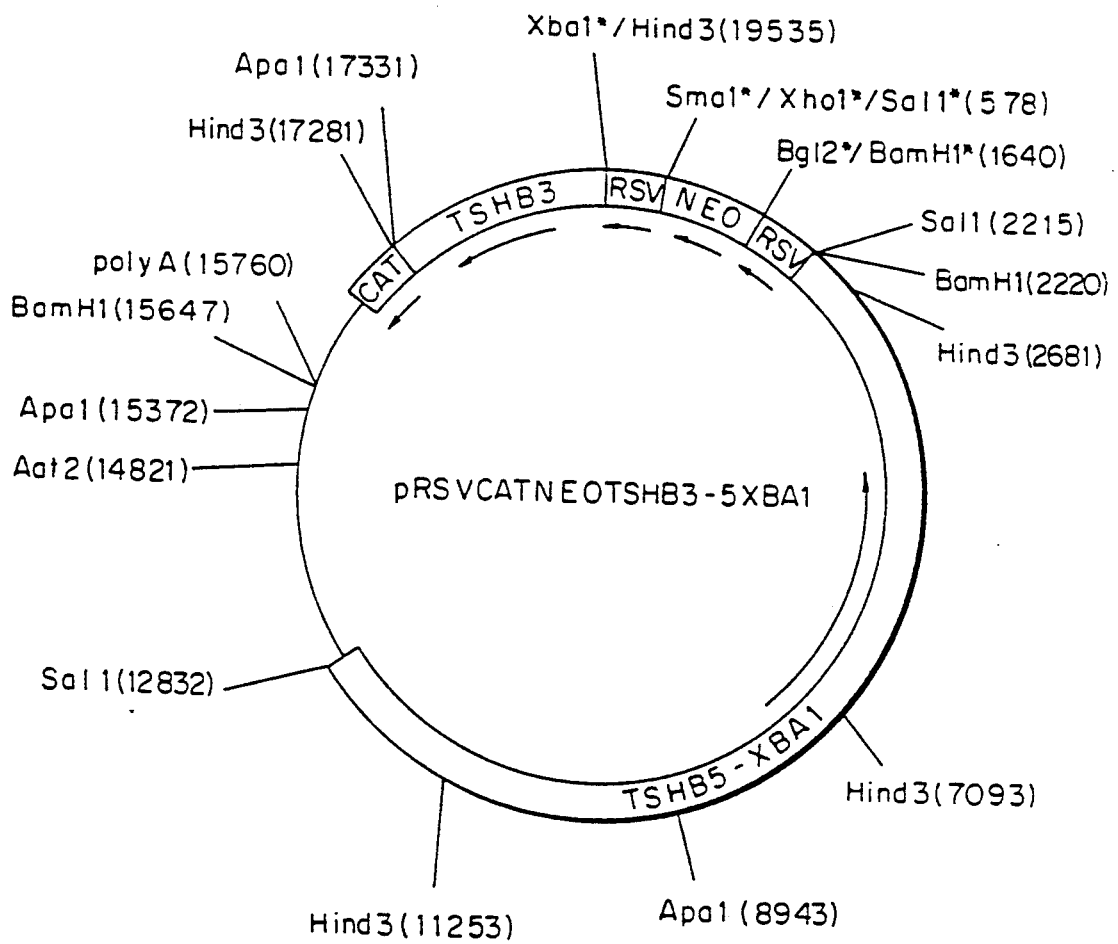
FIG. 13 shows the construction of the pRSVCAT-NEOTSHB3-5XbaI plasmid, including the restriction sites thereof.

The subcloned 10.6 kb XbaI fragment from the rat TSH$\beta$ clone (FIG. 11) was isolated and the XbaI ends converted to SalI sites by blunt ending the fragment with DNA polymerase I Klenow fragment and attaching SalI linkers. This 10.6 kb SalI fragment was then cloned into the SalI site of pRSVCATNEOTSHB3 (FIG. 12). A plasmid containing the insert in the correct orientation was identified and named pRSVCAT-NEOTSHB3-5XbaI (FIG. 13). The latter plasmid has been deposited in the American Type Culture Collection, Rockville, Md., and has received depository number ATCC 40933. For the purpose of this deposit, the plasmid was renamed pHRTSH. This deposit was made in accordance with all of the requirements of the Budapest Treaty.

CELL LINE

GH$_3$ cells are a subcloned population of MtT/W5 which was derived from a radiation induced pituitary tumor in rats (B. K. Takemoto, *Cancer Research*, 22:917 (1962)) and adapted to growth in culture by Tashjian et al., *Endocrinology*, 82:342-352 (1968). The GH$_3$ cells were obtained from the American Type Culture Collection cell bank and are maintained in culture by growth in Dulbecco's Modified Eagle's Medium (DMEM)+15% horse serum (HS)+2.5% fetal bovine serum (FBS)+1% L-glutamine (GH$_3$ media) at 37° C. in 5% CO$_2$.

DNA PREPARATION

Large-Scale Preparation of Plasmid DNA

All plasmids used for stable transfections were purified by using the alkaline lysis method for large-scale plasmid DNA purification as described in *Current Protocols in Molecular Biology*, vol. 1, pp. 1.7.1-1.7.2. DNA isolated by the alkaline lysis method was further purified by double banding in a cesium chloride gradient as also described in *Current Protocols in Molecular Biology*, vol. 1, pp. 1.7.5-1.7.7.

Prior to transfection, the HR vectors were digested with either AatII or ApaI. ApaI was used to linearize the control plasmid pRSVCATNEO and AatII to linearize the HR plasmid pRSVCATNEOTSHB3-5XbaI. The location of the cleavage sites of ApaI and AatII can be seen in FIGS. 10 and 13 respectively. After digestion with the appropriate restriction enzyme, the reaction was phenol/chloroform extracted, chloroform extracted, ethanol precipitated, and washed once with 70% ethanol. The plasmids were then resuspended in sterile deionized water (dH$_2$O) to a concentration of 1 microgram/microliter ($\mu$g/$\mu$l) as determined by absorbance at OD$_{260}$. In an attempt to increase the transfection efficiency and/or the ratio of homologous recombination positives to those that were due to random integration, pRSVCATNEOTSHB3-5XbaI was digested with ApaI. Digestion with ApaI cuts at three separate sites in pRSVCATNEOTSHB3-5XbaI and removes all regions of the vector except those necessary for homologous recombination (FIG. 13). After digestion with ApaI, the reaction was electrophoresed on a 0.8% agarose gel and the top band corresponding to the 10,992 bp fragment containing the two 5' flanking regions of the TSH$\beta$ gene, the RSV promoter - NEO region and the TSH$\beta$ gene-activating RSV promoter was isolated from the gel by electroelution into dialysis tubing. The electroeluted DNA was further purified by using an elutip minicolumn (Schleicher and Schuell) with the manufacturer's recommended standard protocol. The DNA was eluted from the column, ethanol precipitated, washed with 70% ethanol and resuspended to a concentration of 1 $\mu$g/$\mu$l.

STABLE TRANSFECTIONS

Calcium Phosphate Transfection 48 hours prior to transfection 3×10$^6$ GH$_3$ cells were plated on 10 centimeter (cm) dishes. For each dish, 10 $\mu$g of vector DNA along with 30 $\mu$g of sonicated salmon sperm DNA was added to 0.5 milliliters (ml) of tranfection buffer. The transfection buffer was prepared by combining 4g NaCl, 0.185g Kcl, 0.05g Na$_2$HPC$_4$, 0.5 g dextrose, 2.5 g HEPES and dH$_2$O to a final volume of 500 ml and bringing the pH to 7.5. 31 $\mu$l of 2 molar (M) CaCl$_2$ was added to the 0.5 ml of DNA+transfection buffer and vortexed. This solution was allowed to stand at room temperature for 45 minutes. When the DNA-CaCl$_2$-transfection buffer was ready, the GH$_3$ medium was removed from the GH$_3$ cells and the DNA-CaCl$_2$-transfection buffer was layered over the cells. The cells were allowed to stand at room temperature for 20 minutes. After 20 minutes, 5 ml of GH$_3$ medium was added and the plates were incubated at 37° C. for 6 hours. The cells were then shocked by aspirating off the medium and adding 5 ml of fresh transfection buffer containing 15% glycerol for 3.5 minutes. The cells were rinsed 2× with PBS and fed with 10 ml of GH$_3$ medium. 48 hours post-transfection, the medium was removed and 10 ml of GH$_3$ medium containing 400 $\mu$g/ml G418 was added.

Electrocoration

Electroporation was carried out using a BTX 300 Transfector with 3.5 millimeter (mm) gap electrodes. 1×10$^7$ GH$_3$ cells growing in log phase were removed from their plates by trypsinization, pelleted by centrifugation and washed once with PBS. Cells were resuspended in 1.0 ml of PBS and transferred to 2.9 ml Ultra-UV disposable cuvettes (American Scientific Products) on ice. 10 $\mu$g of DNA was added to the cells, mixed and placed back on ice for 5 minutes. After 5 minutes the electrodes were placed in the chamber and the cells were electroporated at a setting of 750 microfarads with a 200 volt pulse. The cuvette was then returned to ice for 10 minutes. Cells were transferred from the cuvette to 9 ml of GH$_3$ medium containing 1% penicillin and 1% streptomycin at room temperature in a 15 ml conical tube and allowed to stand for 10 minutes. The total electroporation of 1×10$^7$ cells was transferred to three 10 cm plates giving approximately 3×10$^6$ cells per plate. After 48 hours, the GH$_3$ medium containing 400 $\mu$g/ml G418 was added.

Transfection of GH$_3$ cells with pRSVCATNEOTSHB3-5XbaI (AatII cut). oRSVCATNEOTSHB3-5XbaI (ApaI cut) and oRSVCATNEO (ApaI cut)

pRSVCATNEOTSHB3-5XbaI (AatII cut), pRSVCATNEOTSHB3-5XbaI (ApaI cut) and pRSVCATNEO (ApaI cut) plasmids were transfected into GH$_3$ cells along with a no DNA control using both the calcium phosphate protocol and the electroporation protocol. 48 hours after transfection, the cells were put under G418 selection. Approximately 14 to 21 days later the colonies became visible by eye on the 10 cm dishes and were counted. In all of the no DNA controls, there were no visible colonies, demonstrating that the G418 selection was working and that the presence of a plasmid containing the RSV-NEO region was necessary to confer G418 resistance. At this time, colonies were picked and pooled by isolating regions on the 10 cm dish with 17 millimeter wide cloning rings. These large cloning rings encompassed between 10 and 70 colonies depending on the density of the colonies per plate and allowed the GH$_3$ cells in that isolated region to be removed and pooled at the same time by trypsination. The trypsinized colonies in each ring were transferred to 6 well plates and allowed to grow in GH$_3$ media containing G418. After reaching 70% to 80% confluence, 80,000 cells were transferred to a 24 well plate and the remaining cells cryopreserved for further testing at a later date. The cells in the 24 well plates were grown until they reached 50% to 80% confluence Total RNA was then harvested from these GH$_3$ cells by the following procedure.

RNA ISOLATION FROM TRANSFECTED GH$_3$ CELLS GROWN IN 24 WELL PLATES

The following is a modification of the protocol described by Chomczynski and Sacchi, *Anal. Biochem.*, 162:156–159 (1987). The media covering the GH$_3$ cells in the 24 well plates was removed and the cells washed with 1 ml of PBS. 1 ml of GTC solution was added and the cells were incubated at room temperature for 5 minutes. GTC I5 solution was prepared by dissolving 250 g of guanidium thiocyanate (Fluka) in 293 ml of dH$_2$O, and then adding 17.6 ml of 0.75 M Na citrate pH 7.0 and 26.4 ml of 10% sarcosyl (L-Lauryl sarcosine). Just prior to use, 360 $\mu$l of $\beta$-mercaptoethanol per 50 ml GTC solution was added. After 5 minutes at room temperature, the 1 ml of GTC-cell lysate was transferred to a Sarstedt 55.518 snap-cap tube containing 2 ml of GTC solution. To each tube was added 300 $\mu$l of 2M sodium acetate pH 4.0 and the tube vortexed. Next, 3 ml of dH$_2$O saturated phenol was added and the tubes were vortexed again. To each tube was added 600 $\mu$l of chloroform:isoamyl alcohol (49:1) and the tube was shaken by hand for 10 seconds and placed on ice for 15 minutes. The tubes were then centrifuged in a Sorval RC-5B using a SM24 rotor at 8000 revolutions per minute (RPM) for 20 minutes at 4° C. The aqueous phase was transferred to a fresh Sarstedt tube containing 3 ml of isopropanol and placed at −20° C. for 1 hour. After 1 hour the tubes were spun in a Sorval RC-5B using a SM24 rotor at 8000 rpm for 20 minutes at 4° C. The supernatants were removed and the pellets resuspended in 500 μl of GTC solution. The resuspended RNA was transferred to a 1.5 ml eppendorf tube to which 500 μl of isopropanol was added. The tubes were once again placed at −20° C. for 1 hour. The eppendorf tubes were spun for 5 minutes in a microfuge and the supernatant discarded. The pellet was washed with 70% ethanol 2 times and allowed to dry until the ethanol had completely evaporated. The pellet was resuspended in 20 μl of diethyl pyrocarbonate (depc) treated water and heated to 65° C. for 5 minutes. This RNA was then used to make cDNA in one of the two procedures described below.

cDNA REACTIONS

Method 1

First strand cDNA was synthesized from 2.5–6.0 microliters of total RNA (approximately 0.5–6 micrograms) in a reaction volume of 10–20 microliters. The total RNA was obtained by the extraction method described above, and was denatured for 5–10 minutes at 70° C. and quick chilled on ice before adding the reaction components. The reaction conditions were 50 millimolar (mM) Tris-HCl (pH 8.3), 10 mM MgCl$_2$, 10 mM DTT, 0.5 mM each of dCTP, dATP, dGTP, and dTTP (Pharmacia), 40 mM KCl, 500 units/ml RNasin (Promega Biotech), 85 μg/ml oligo(dT)$_{12-18}$ (Collaborative Research, Inc.), and 15,000–20,000 units/ml Moloney murine leukemia virus reverse transcriptase (Bethesda Research Laboratories) incubated at 37° C. for 60 minutes. The reaction was terminated by the addition of EDTA to 40 mM, and the nucleic acid was precipitated by adding sodium acetate to a concentration of 0.3 M and two volumes of ethanol. The precipitate was allowed to form at 0° C. for 30 minutes and was pelleted by centrifugation in a microfuge at 14,000 rpm for thirty minutes. The pellet was washed with 70% ethanol, dried, and resuspended in depc treated water to a volume of 15–25 microliters.

Method 2

Conditions for first strand synthesis of cDNA from RNA were adapted from Carol A. Brenner et al, BioTechniques, Vol. 7, No. 10, pp. 1096–1103 (1989). 1 μl of total RNA from the RNA prep procedure described above was added to 9 μl of reaction buffer in a 0.5 ml eppendorf tube. The reaction buffer consisted of 200 units of Moloney murine leukemia virus reverse transcriptase (MMLVRT Bethesda Resesarch Labs), and a final concentration of the following reagents: 70 mM Tris.HCl pH 8.8, 40 mM KCl, 0.1% Triton X-100, 1 mM of each dNTP, 4 mM MgCl$_2$, and 0.45 OD$_{260}$ units of random hexamers (Pharmacia). After mixing, the tubes were incubated at room temperature for 10 minutes and then placed at 42° C. for 1 hour. After 1 hour the tubes were heated to 90° C. for 1 minute to deactivate the MMLVRT and then cooled to room temperature.

POLYMERASE CHAIN REACTION (PCR) AMPLIFICATION OF RNA FROM GH$_3$ CELLS

The following primers were used to amplify, by PCR, TSHβ cDNA synthesized from RNA transcripts produced by the GH$_3$ cells as a result of the HR plasmids activating the endogenous TSHβ gene by homologous recombination.

| primer | 5'                         3' |
|--------|-------------------------------|
| TSHβ5  | AGTATATGATGTACGTGGACAGG       |
| TSHβ3  | CACTTGCCACACTTGCAGCTCAGG      |

FIG. 14 shows the regions of the TSHβ gene to which each primer corresponds.

PCR REACTION CONDITIONS

All PCR reactions were performed in the Ericomp Twinblock thermocycler. If PCR amplification was to be run on cDNA made by method 2, 40 μl of additional reaction mix was directly added to the 10 μl of the cDNA reaction bringing the total volume up to 50 μl. The final concentrations of reagents in the 50 μl were 70 mM Tris.HCl pH 8.8, 40 mM KCl, 0.1% Triton X-100, 2.25 units Taq 200 μM each dNTP, and 0.8 mM MgCl$_2$.

If PCR was to be performed on cDNA made by method 1 above, 5 to 10 μl of the resuspended cDNA was added to 40 to 45 μl containing final concentrations of the following: 70 mM Tris.HCl pH 8.8, 40 mM KCl, 0.1% Triton X-100, 2.25 units Taq polymerase, 0.2 μM each primer, 200 μM each dNTP, and 0.8 mM MgCl$_2$.

The reactions were then subjected to the following PCR cycles.
1 minute at 94° C.
30 seconds at 55° C.
2 minutes at 72° C.

The above cycle was repeated 30 to 40 times. 10 μl of each reaction mix was run on a 6% polyacrylamide gel and screened for the presence of a 247 bp PCR fragment which would indicate the presence of the properly spliced mRNA for TSHβ

PCR RESULTS FOR AMPLIFICATION OF TSHβ RNA FROM GH$_3$ CELLS AND RAT PITUITARY GLAND TOTAL RNA

To determine whether GH$_3$ cells normally synthesize TSHβ RNA, cDNA from untransfected GH$_3$ cells as well as cDNA from rat pituitary glands was subjected to the above PCR reaction conditions. The correct 247 bp band indicative of the presence of TSHβ mRNA was visible in the positive control of the rat pituitary gland sample but no band was visualized from the GH$_3$ cell total RNA sample even after 60 cycles (data not shown).

TRANSFECTION RESULTS

The number of G418 resistant colonies present on the 10 cm dishes were tabulated between 14 and 21 days after addition of G418 to the media.

| Transfection Method | Colonies per 10 cm dish | | |
|---|---|---|---|
| | pRSVCATNEO | pRSVCATNEOTSHB3-5XBA1 | |
| | | ApaI cut | AatII cut |
| Calcium phosphate 1 | 48 | 13 | 29 |
| Calcium phosphate 2 | — | 21 | 58 |
| Electroporation 1 | — | 1295 | 415 |
| Electroporation 2 | — | 1051 | 723 |

Total RNA was harvested from the colony pools contained in the 24 cell plates as described above. cDNA was made from these RNA preps and subjected to PCR amplification. The number of positive colonies producing TSHβ mRNA was determined by the presence of a 247 bp fragment as visualized on a polyacrylamide gel. Each of the pools screened contained between 10 and 70 colonies. The estimated number of colonies per pool per transfection was used to approximate the number of G418 resistant GH3 cell clones in which TSHβ gene transcription was activated. If a pool tested positive, it was assumed that this represented one positive colony present in that particular pool.

| plasmid | G418 resistant colonies | TSHβ RNA positive |
|---|---|---|
| pRSVCATNEO | 60 | 0 |
| pRSVCATNEOTSHB3-5XBA1 (Aat2 digested) | 4942 | 3 |
| pRSVCATNEOTSHB3-5XBA1 (ApaI digested) | 8580 | 6 |

These results demonstrate the successful activation of the normally transcriptionally silent TSHβ gene by the method of the present invention. While the number of colonies that are positive for TSHβ transcription is small compared to the number of colonies that are G418 resistant (approximately one out of every $10^3$ G418 resistant colonies), this result is generally consistent with rates reported for other homologous recombination experiments (Michael Kriegler, *Gene Transfer and Expression A Laboratory Manual*, Stockton Press, New York, N.Y. (1990), pp. 56–60). It has been generally observed that the homologous recombination rate seems to be proportional to the rate of transcription of the targeted gene (M. Frohman and G. Martin, *Cell*, 56:145 (1989); S. L. Mansour et al, *Nature*, 336:348 (1988)). It should be noted that the rate which has been demonstrated is three orders of magnitude higher than what might be expected for random mutation turning on the TSHβ gene.

Figure 15:
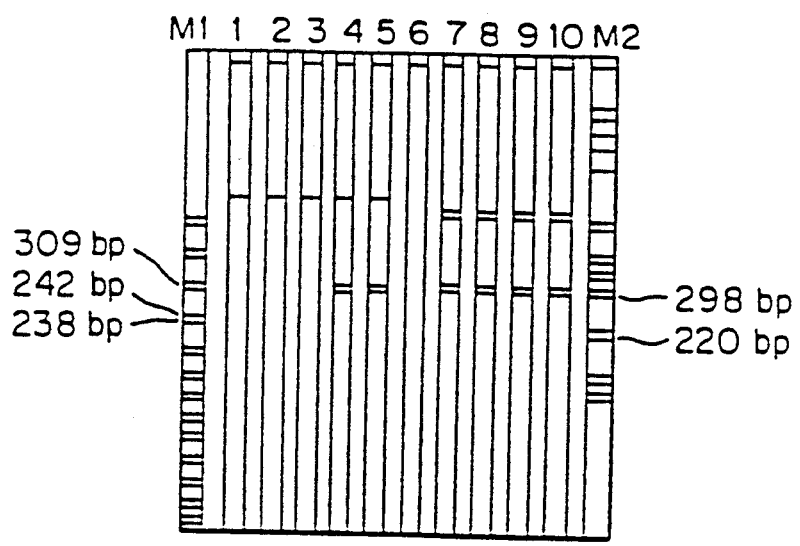

To ensure that the results for each colony pool were reproducible and that the activation of RNA transcription was stable, colony pools previously frozen away corresponding to pools which tested positive in the first screening were thawed and expanded in culture. The freshly thawed GH3 positive pools were seeded in T 25 tissue culture flasks and expanded until the cells reached 70% to 80% confluence. 80,000 cells were then plated in 24 well plates from each flask and grown until they were 50% to 70% confluent. RNA was extracted from the cells, converted into cDNA, and screened once again for the presence of TSHβ RNA by running 10 μl of each PCR reaction on a 6% polyacrylamide gel. FIG. 15 shows the results of representative PCR reactions from the second screening as visualized on a polyacrylamide gel by ethidium bromide staining and fluorescence. Lanes 1, 2, and 3 contain the PCR reactions run on cDNA from GH3 cells which had been transfected by pRSVCATNEO. pRSVCATNEO contains no regions of homology to TSHβ and thus is not capable of activating the TSHβ gene by homologous recombination. As can be seen on the gel in FIG. 15, there are no bands corresponding to 247 bp in those lanes indicating that the TSHβ gene is not activated. Lane 6 also contains a negative control. In that lane three pools were combined from samples of GH3 cells which had been transfected with pRSVCATNEOTSHB3-5XbaI (ApaI cut) but which were negative for transcription of the TSHβ gene on the first screening. The absence of the 247 bp fragment in lane 6 demonstrates that the presence of the transfected pRSVCATNEOTSHB3-5XbaI (ApaI cut) plasmid integrated randomly in the genome is not capable of producing the 247 bp TSHβ PCR fragment. Lanes 7, 8, 9, and 10 include PCR reactions run on cDNA made from total RNA harvested from rat pituitary glands in quantities per reaction of 25 nanograms, 100 nanograms, 200 nanograms, and 400 nanograms, respectively. The presence in these lanes of the expected 247 bp band, produced from cDNA prepared from a rat tissue which normally expresses TSHβ, showed that the PCR reaction conditions were correctly optimized and that the PCR band obtained in lanes 4 an 5 containing the homologous recombination TSHβ positives is of the correct size. Two pools transfected with pRSVCATNEOTSHB3-5XbaI (ApaI cut) which were positive in the first screening, ApaI-107 in lane 4 and ApaI-136 in lane 5, once again tested positive for TSHβ gene activation as demonstrated by the presence of the correct TSHβ PCR band amplified from cDNA made from the total RNA extracts from those pools proving that transcription of TSHβ gene has been stably activated. The presence of bands at 247 bp in lanes 4 and 5 containing RNA from previous positives ApaI-107 and ApaI-136 and the absence of bands in the negative controls of pRSVCATNEO transfected GH3 cells in lanes 1–3 and the pRSVCATNEOTSHB3-5XbaI (ApaI cut) negatives in lane 6 demonstrated that the production of TSHβ RNA in a cell line that does not normally produce that RNA has been stably turned on by homologous recombination.

The present invention is not limited to the cell line that is described herein. All cell lines have genetic information which is normally silent or inert. Most are able to express only certain genes. However, a normally transcriptionally silent or inert gene of any such cell line can be activated to express the gene product in accordance with the present invention and any gene of the genome may have its expression characteristics modified in accordance with the present invention. Even previously transformed cell lines can be used as long as the previous transformation did not disrupt the gene of interest. The source of the cell line is not important. The cell line may be animal or plant, primary, continuous or immortal. Of course, it is desirable that any such cell line be stable and immortal so that after treatment with the technique in accordance with the present invention, expression can be commercialized. Cloned microorganisms, whether prokaryotic or eukaryotic, may also be treated by the technique of the present invention.

While the present invention has been preferably described with respect to the expression of a normally transcriptionally silent or inert gene, the technique of the present invention is also applicable to the modification of the expression characteristics of a gene which is naturally expressed in the host cell line. For example, if it is desired to render the expression of a gene dependent upon culture conditions or the like so that expression can be turned on and off at will, an appropriate DNA regulatory segment, such as a regulatable promoter, can be inserted which imparts such characteristics, such as repressibility or inducibility. For example, if it is known that the cell type contains nuclear steroid receptors, such as estrogen, testosterone or glucocorticoid, or thyroxin receptors, one could use the steroid or thyroxin response elements as region F. Such a response element is any DNA which binds such receptor to elicit a positive response relative to transcription. Even if a cell is not naturally responsive to glucocorticoids, for example, a piece of DNA which encodes the glucocorticoid receptor could be added to the construct, or otherwise inserted somewhere in the genome, so as to make the cell responsive to glucocorticoids. The use of a regulatable promoter could be desirable whether or not the gene of interest is normally transcriptionally silent. Other kinds of regulation can also be obtained by targeting the appropriate DNA regulatory segment to the exact position of interest by means of the process of the present invention.

Thus, while stimulation of expression of normally transcriptionally silent genes is the preferred application of the present invention, in its broadest sense it is applicable to the modification of expression characteristics of any gene endogenous to the host cell line.

The specific technique of homologous recombination is not, per se, a novel part of the present invention. Such techniques are known and those of ordinary skill in this art will understand that any such technique can be used in the present invention as long as it permits targeting of the DNA regulatory sequence to the desired location with respect to the gene of interest. While a preferred technique is disclosed, using a linearized construct with two homologous regions on either end of the sequences to be inserted, any other technique which will accomplish this function, as, for example, by using circular constructs, is also intended to be comprehended by the present invention. The critical feature of the present invention is the use of homologous recombination techniques to insert a DNA regulatory sequence which causes modification of expression characteristics in the cell line or microorganism being used, operatively linked with a gene in the genome of the cell line, preferably one which is normally transcriptionally silent, or to insert an amplifiable sequence, without a regulatory sequence, sufficiently near a gene in the genome of the cell line which already transcribes as to cause amplification of such gene upon amplification of the amplifiable sequence. It is not absolutely necessary that a selectable marker also be included. Selection can be based solely on detection of the gene product of interest or mRNAs in the media or cells following insertion of the DNA construct. Furthermore, in the embodiment in which a regulatory sequence is being inserted, amplification, while desired, is not critical for operability. The same is true for the negative selection gene which makes the screening process easier, but is not critical for the success of the invention. Thus, the basic embodiment requires only insertion of the DNA regulatory segment or the amplifiable segment in the specific position desired. However, the addition of positive and/or negative selectable marker genes for use in the selection technique is preferred, as is the addition of an amplifiable gene in the embodiment in which a regulatory segment is being added.

The term "modification of expression" as used throughout the present specification and claims, is hereby defined as excluding termination of expression by inserting by homologous recombination a mutation, deletion, stop codon, or other nucleotide sequence, including an entire gene, into the gene of interest, so as to prevent the product of interest from being expressed. The prior art teaches the use of homologous recombination to insert specific mutations and the expression of a cell product may have inherently been terminated by means thereof (see, for example, Schwartzberg et al, PNAS (USA), 87:3210-3214 (1990)). The present invention is not intended to encompass such a procedure. In the present invention the "modification of expression" is accomplished by means of inserting regulatory and/or amplification regions at a specific desired location by means of homologous recombination. The preferred modifications are those which activate and/or enhance expression of the product of interest.

Whenever the present specification uses the phrase that a DNA regulatory segment is "operatively linked with" a gene, such terminology is intended to mean that the DNA regulatory segment is so disposed with respect to the gene of interest that transcription of such gene is regulated by that DNA regulatory segment The regulatory segment is preferably upstream of the gene, but may be downstream or within the gene, provided that it operates to regulate expression of the gene in some way. The DNA regulatory segment may be a promoter, terminator, operator, enhancer, silencer, attenuator, or the like, or any combination thereof.

Whenever the terms "upstream" or "downstream" are used in the present specification and claims, this is intended to mean in the 5'-direction or the 3'-direction, respectively, relative to the coding strand of the gene of interest.

The foregoing description of the specific embodiments so fully reveals the general nature of the invention that others can readily modify and/or adapt such specific embodiments for various applications without departing from the generic concept. Any such adaptations and modifications are intended to be embraced within the meaning and range of equivalents of the disclosed embodiments. It is to be understood that the phraseology and terminology employed herein are for the purpose of description and not of limitation.

What is claimed is:

1. A method of activating a predetermined normally transcriptionally silent gene within the genome of a cell line so as to enable said cell line to express the gene product of said gene, comprising inserting a DNA construct into said genome by homologous recombination, said DNA construct comprising a DNA regulatory segment capable of stimulating expression of said gene when operatively linked thereto and a DNA targeting segment homologous to a region of said genome within or proximal to said gene, wherein said construct is inserted such that said regulatory segment is operatively linked to said gene of interest.

2. A method of modifying, the expression characteristics of predetermined a gene within the genome of a cell line, comprising inserting a DNA construct into said genome by homologous recombination, said DNA construct comprising a DNA regulatory segment capable of modifying the expression characteristics of said gene when operatively linked thereto, as compared to its existing DNA regulatory segment, and a DNA targeting segment homologous to a region of said genome within or proximal to said gene, wherein said construct is inserted such that said regulatory segment is operatively linked to said gene of interest.

3. A method of modifying the expression characteristics of a predetermined gene within the genome of a cell line, comprising inserting a DNA construct into said genome by homologous recombination, said DNA construct comprising an expressible, amplifiable gene capable of amplifying said gene when inserted in sufficiently close proximity thereto, and a DNA targeting segment homologous to a region of said genome within or proximal to said gene, wherein said construct is inserted such that said amplifiable gene is in sufficiently close proximity to said gene of interest to cause amplification thereof when said amplifiable gene is amplified.

4. A method in accordance with claim 3, wherein said DNA construct additionally comprises at least one expressible selectable marker gene disposed so as to be inserted with said expressible, amplifiable gene.

5. A method in accordance with claim 1, 2 wherein said DNA construct comprises two DNA targeting segments, each homologous to a region of said genome within or proximate to said gene, one of said targeting segments being upstream of said regulatory segment and the other of said targeting segments being downstream of said regulatory segment.

6. A method in accordance with claim 1, wherein said DNA construct additionally comprises at least one expressible selectable marker gene disposed so as to be inserted with said regulatory segment.

7. A method in accordance with claim 1, wherein said DNA construct additionally comprises a negative selectable marker gene disposed with respect to said targeting segment so as not to be inserted when said construct is properly inserted by homologous recombination, whereby said negative selectable marker is not expressed in cells in which said DNA construct is properly inserted.

8. A method in accordance with claim 1, wherein said DNA construct additionally comprises an expressible amplifiable gene disposed so as to be inserted with said regulatory segment.

9. A method in accordance with claim 1, wherein said cell line is a eukaryotic cell line.

10. A method in accordance with claim 9, wherein said cell line is an animal cell line.

11. A method in accordance with claim 9, wherein said cell line is a mammalian cell line.

12. A method in accordance with claim 9, wherein said cell line is a plant cell line.

13. A method in accordance with claim 6, and additionally for causing expression of said gene product, further including the steps of, following said inserting step:
selecting clones of said cell line which express the product of said selectable marker gene;
cultivating the selected clones under conditions sufficient to permit expression of said gene product; and collecting said gene product.

14. A method in accordance with claim 13, wherein said selectable marker gene is the neomycin resistance gene and said selecting step comprises selecting those clones having neomycin resistance.

15. A method in accordance with claim 13 wherein said DNA construct additionally comprises a negative selectable marker gene disposed with respect to said targeting segment so as not to be inserted when said construct is properly inserted by homologous recombination, whereby said negative selectable marker is not expressed in cells in which said DNA construct is properly inserted, and said selecting step further includes selecting those clones which do not express said negative selectable marker gene.

16. A method in accordance with claim 15 wherein said negative selectable marker gene is the Herpes Simplex Virus thymidine kinase gene and said selecting step includes selecting those clones which survive exposure to a medium that kills cells which express said gene.

17. A genome of a cell line, the genome having a DNA regulatory segment operatively linked with a predetermined naturally occurring gene at an insertion site characterized by a predetermined DNA sequence, said DNA regulatory segment not being naturally occurring at said location in the genome.

18. A cell line capable of expressing a gene product by a predetermined normally transcriptionally silent gene within the genome of said cell line, said genome having inserted therein a DNA regulatory segment operatively linked with said normally transcriptionally silent gene, said DNA regulatory segment being capable of promoting the expression of a gene product by said cell line.

19. A cell line capable of enhanced expression of a gene product compared to the cell line from which it is derived, said gene product being the expression product of predetermined an endogenous gene within the genome of said cell, said genome having inserted therein in an operative manner, at or near said endogenous gene, an exogenous DNA regulatory segment and/or amplifiable gene capable of enhancing the expression of said gene product by said cell line.

20. A cell line in accordance with claim 19, wherein said exogenous DNA regulatory segment and/or amplifiable gene is an exogenous DNA regulatory segment.

21. A cell line in accordance with claim 19, wherein said exogenous DNA regulatory segment and/or amplifiable gene is an exogenous amplifiable gene.

22. A cell line in accordance with claim 18 wherein said DNA regulatory segment is one which is capable of promoting the expression of a gene product normally expressed by said cell line.

23. A cell line in accordance with claim 22, wherein the inserted DNA regulatory segment is part of a DNA construct comprising said DNA regulatory segment and at least one selectable marker gene.

24. A cell line in accordance with claim 23, wherein said DNA construct additionally comprises an amplifiable gene.

25. A method of obtaining a gene product from a cell line, comprising culturing a differentiated a cell line in accordance with claim 18 under conditions which permit expression of said gene product, and collecting said gene product.

26. A DNA construct for insertion into a predetermined host cell line, comprising a DNA regulatory segment capable of modifying the expression characteristics of genes in the host cell line when operatively linked thereto and a DNA targeting segment homologous to a region of the genome of a preselected gene within the host cell line.

27. A DNA construct for insertion into a predetermined host cell line, comprising an expressible, amplifiable gene capable of amplifying a gene in the host cell line when inserted in sufficiently close proximity thereto, and a DNA targeting segment homologous to a region of the genome of a preselected gene within the host cell line.

28. A method in accordance with claim 2, wherein said DNA construct comprises two DNA targeting segments, each homologous to a region of said genome within or proximate to said gene, one of said targeting segments being upstream of said regulatory segment and the other of said targeting segments being downstream of said regulatory segment.

29. A method in accordance with claim 2, wherein said DNA construct additionally comprises at least one expressible selectable marker gene disposed so as to be inserted with said regulatory segment.

30. A method in accordance with claim 2, wherein said DNA construct additionally comprises a negative selectable marker gene disposed with respect to said targeting segment so as not to be inserted when said construct is properly inserted by homologous recombination, whereby said negative selectable marker is not expressed in cells in which said DNA construct is properly inserted.

31. A method in accordance with claim 2, wherein said DNA construct additionally comprises an expressible amplifiable gene disposed so as to be inserted with said regulatory segment.

32. A method in accordance with claim 2, wherein said cell line is a eukaryotic cell line.

33. A method in accordance with claim 32, wherein said cell line is an animal cell line.

34. A method in accordance with claim 32, wherein said cell line is a mammalian cell line.

35. A method in accordance with claim 32, wherein said cell line is a plant cell line.

36. A method in accordance with claim 29, and additionally for causing expression of said gene product, further including the steps of, following said inserting step:
    selecting clones of said cell line which express the product of said selectable marker gene;
    cultivating the selected clones under conditions sufficient to permit expression of said gene product; and
    collecting said gene product.

37. A method in accordance with claim 36, wherein said selectable marker gene is the neomycin resistance gene and said selecting step comprises selecting those clones having neomycin resistance.

38. A method in accordance with claim 36, wherein said DNA construct additionally comprises a negative selectable marker gene disposed with respect to said targeting segment so as not to be inserted when said construct is properly inserted by homologous recombination, whereby said negative selectable marker is not expressed in cells in which said DNA construct is properly inserted, and said selecting step further includes selecting those clones which do not express said negative selectable marker gene.

39. A method in accordance with claim 38, wherein said negative selectable marker gene is the Herpes Simplex Virus thymidine kinase gene and said selecting step includes selecting those clones which survive exposure to a medium that kills cells which express said gene.

40. A method in accordance with claim 3, wherein said DNA construct comprises two DNA targeting segments, each homologous to a region of said genome within or proximate to said gene, one of said targeting segments being upstream of said regulatory segment and the other of said targeting segments being downstream of said regulatory segment.

41. A method in accordance with claim 3, wherein said DNA construct additionally comprises at least one expressible selectable marker gene disposed so as to be inserted with said regulatory segment.

42. A method in accordance with claim 3, wherein said DNA construct additionally comprises a negative selectable marker gene disposed with respect to said targeting segment to as not to be inserted when said construct is properly inserted by homologous recombination, whereby said negative selectable marker is not expressed in cells in which said DNA construct is properly inserted.

43. A method in accordance with claim 3, wherein said DNA construct additionally comprises an expressible amplifiable gene disposed so as to be inserted with said regulatory segment.

44. A method in accordance with claim 3, wherein said cell line is a eukaryotic cell line.

45. A method in accordance with claim 44, wherein said cell line is an animal cell line.

46. A method in accordance with claim 44, wherein said cell line is a mammalian cell line.

47. A method in accordance with claim 44, wherein said cell line is a plant cell line.

48. A method in accordance with claim 41, and additionally for causing expression of said gene product, further including the steps of, following said inserting step:
    selecting clones of said cell line which express the product of said selectable marker gene;
    cultivating the selected clones under conditions sufficient to permit expression of said gene product; and
    collecting said gene product.

49. A method in accordance with claim 48, wherein said selectable marker gene is the neomycin resistance gene and said selecting step comprises selecting those clones having neomycin resistance.

50. A method in accordance with claim 48, wherein said DNA construct additionally comprises a negative selectable marker gene disposed with respect to said targeting segment so as not to be inserted when said construct is properly inserted by homologous recombination, whereby said negative selectable marker is not expressed in cells in which said DNA construct is properly inserted, and said selecting step further includes selecting those clones which do not express said negative selectable marker gene.

51. A method in accordance with claim 50, wherein said negative selectable marker gene is the Herpes Simplex Virus thymidine kinase gene and said selecting step includes selecting those clones which survive exposure to a medium that kills cells which express said gene.

52. A cell line in accordance with claim 20, wherein said DNA regulatory segment is one which is capable of promoting the expression of a gene product normally expressed by said cell line.

53. A method of obtaining a gene product from a cell line, comprising culturing a cell line in accordance with claim 19 under conditions which permit expression of said gene product, and collecting said gene product.

54. A method of obtaining a gene product from a cell line, comprising culturing a cell line in accordance with claim 20 under conditions which permit expression of said gene product, and collecting said gene product.

55. A method of obtaining a gene product from a cell line, comprising culturing a cell line in accordance with claim 21 under conditions which permit expression of said gene product, and collecting said gene product.

56. A method of obtaining a gene product from a cell line, comprising culturing a cell line in accordance with claim 22 under conditions which permit expression of said gene product, and collecting said gene product.

57. A method of obtaining a gene product from a cell line, comprising culturing a cell line in accordance with claim 23 under conditions which permit expression of said gene product, and collecting said gene product.

58. A method of obtaining a gene product from a cell line, comprising culturing a cell line in accordance with claim 24 under conditions which permit expression of said gene product, and collecting said gene product.

* * * * *

UNITED STATES PATENT AND TRADEMARK OFFICE
CERTIFICATE OF CORRECTION

PATENT NO.    : 5,272,071
DATED         : December 21, 1993
INVENTOR(S)   : Scott C. Chappel It is certified that error appears in the above-identified patent and that said Letters Patent is hereby corrected as shown below:

Column 26,
Line 57, after "modifying", delete the comma.
Line 58, delete "predetermined a" and insert therefore -- a predetermined --.

Column 27,
Line 17, delete "2".

Column 28,
Line 25, delete "predetermined an" and insert therefor -- a predetermined --.
Line 38, after "18", add a comma.
Line 50, after "differentiated", delete "a".

Signed and Sealed this

Twenty-seventh Day of May, 2003

JAMES E. ROGAN
*Director of the United States Patent and Trademark Office*

Adverse Decision in Interference

Patent No. 5,272,071, Scott C. Chappel, METHOD FOR THE MODIFICATION OF THE EXPRESSION CHARACTERISTICS OF AN ENDOGENOUS GENE OF A GIVEN CELL LINE, Interference No. 105,114, final judgment adverse to the patentees rendered June 24, 2004, as to claims 1, 2, 5-7, 9-20, 22, 23, 25, 26, 32-39, 52-54, 56, and 57.

(*Official Gazette September 16, 2008*)

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

AGTATATGAT GTACGTGGAC AGG    23

(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

CACTTGCCAC ACTTGCAGCT CAGG    24

(2) INFORMATION FOR SEQ ID NO:3:

(i) SEQUENCE CHARACTERISTICS:
        (A) LENGTH: 999 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

```
GGCACGCCTC TGAATGTGGA AAGGACACTT ATGAGCTCTG TGGTCTTTCC CTCTGATTTA   60
GCATGAATGC TGTCGTTCTC TTTTCCGTGC TTTTCGCTCT TGCTTGTGGG CAAGTGTCAT  120
CGTTTTGTAT TCCCACTGAG TATATGATGT ACGTGGACAG GAGAGAGTGT GCCTACTGCC  180
TGACCATCAA CACCACCATC TGCGCTGGGT ATTGTATGAC ACGGGTATGT TGGTCACTGC  240
GTTTCTTTTA GCTGTAAATT GTACAGGTCT AAAGTTGTCT GTTAATATTT TAGAAAGGAA  300
GTGGGATAAA TCATAGTCTC CTCTTTGGGA AGCCAAGCAC ACTGCTTTCA GAATTATAAT  360
TATGTCATTC TACACAGAAA AAGTACAGAT ACATTGTAAC AGTTTACCCT AAAGTGTTTG  420
TTCTGCTCAA TGGTAGATGA GAAGAAAGTG TCCTTTTTTG TCTCTGAGGG GTTAAGTGTA  480
GATGTGTGGG TAACAGAGCT CAGGAGTCCT TTAAGATCAT CAGGAAACAA AGGGATATTA  540
GTCATTCTAT TACACTAAGT TGCATGCAGT TTATCATGTT AAGATCTCTT TTCTTCCACA  600
GGATATCAAT GGCAAACTGT TTCTTCCCAA GTACGCACTC TCTCAGGATG TCTGTACATA  660
CAGAGACTTC ACCTACAGAA CGGTGGAAAT ACCGGGATGC CCACACCATG TTGCTCCTTA  720
TTTCTCCTAC CCCGTTGCCC TGAGCTGCAA GTGTGGCAAG TGTAACACTG ACTACAGCGA  780
CTGTACACAC GAGGCTGTCA AAACCAACTA CTGCACCAAG CCACAGACAT TCTATCTGGG  840
GGGATTTTCT GGTTAACTGT AATGGCAATG CAATCTGGTT AAATGTGTTT ACCTGGAATA  900
GAACTAATAA AATATCATTG ATATGTCTTG CCTGCCATTT AATCCATAGG CACATCCACA  960
AGGCATTAGA GAGCTTACAC AACTTTAGAA GCAGAGGCG                         999
```